US011390858B2

(12) United States Patent
Tubbs et al.

(10) Patent No.: US 11,390,858 B2
(45) Date of Patent: *Jul. 19, 2022

(54) MODIFIED TEMPLATE-INDEPENDENT ENZYMES FOR POLYDEOXYNUCLEOTIDE SYNTHESIS

(71) Applicant: Molecular Assemblies, Inc., San Diego, CA (US)

(72) Inventors: Julie L. Tubbs, San Diego, CA (US); Prem Sinha, San Deigo, CA (US); Boguslaw Stec, San Diego, CA (US); Christopher Wilson, San Diego, CA (US); J. William Efcavitch, San Carlos, CA (US); Deanne W. Sammond, San Diego, CA (US)

(73) Assignee: Molecular Assemblies, Inc., San Diego, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/891,449

(22) Filed: Jun. 3, 2020

(65) Prior Publication Data

US 2021/0009969 A1    Jan. 14, 2021

Related U.S. Application Data

(63) Continuation-in-part of application No. 16/165,465, filed on Oct. 19, 2018, now Pat. No. 10,774,316, which is a continuation-in-part of application No. 16/113,757, filed on Aug. 27, 2018, now Pat. No. 10,760,063, which is a continuation-in-part of application No. 14/918,212, filed on Oct. 20, 2015, now Pat. No. 10,059,929.

(60) Provisional application No. 62/065,976, filed on Oct. 20, 2014.

(51) Int. Cl.
*C12N 9/12* (2006.01)
*C12P 19/34* (2006.01)

(52) U.S. Cl.
CPC .......... *C12N 9/1264* (2013.01); *C12P 19/34* (2013.01); *C12Y 207/07031* (2013.01)

(58) Field of Classification Search
None
See application file for complete search history.

(56) References Cited

U.S. PATENT DOCUMENTS

| 8,808,989 | B1 | 8/2014 | Efcavitch et al. |
| 10,760,063 | B2* | 9/2020 | Efcavitch ....... C12Y 207/07031 |
| 2004/0043396 | A1 | 3/2004 | Mueller et al. |
| 2011/0081647 | A1 | 4/2011 | Siddiqi et al. |
| 2012/0202196 | A1 | 8/2012 | Balasubramanian et al. |
| 2014/0141414 | A1 | 5/2014 | Liu et al. |
| 2016/0108382 | A1 | 4/2016 | Efcavitch et al. |

FOREIGN PATENT DOCUMENTS

| WO | 2016028802 A1 | 2/2016 |
| WO | 2016128731 A1 | 8/2016 |
| WO | 2018102818 A1 | 6/2018 |

OTHER PUBLICATIONS

Database Uniparc [Online], Jan. 31, 2014, Retrieved from UniProt Database Accession No. UPI0003E329AC (1 Page).
Delarue et al. "Crystal Structures of a Template-Independent DNA Polymerase: Murine Terminal Deoxynucleotidyltransferase," EMBO J. Feb. 1, 2002 (Feb. 1, 2002), vol. 21, pp. 427-439 (13 Pages).
Extended European Search Report issued in European Application No. 19213236.3, dated Jun. 17, 2020 (21 pages).
Extended European Search Report issued in European Application No. 15851895.1, dated Mar. 9, 2018 (7 Pages).
International Search Report and Written Opinion issued in International Patent Application No. PCT/U2019/57014, dated Feb. 4, 2020 (9 pages).
International Serach Report and Written Opinion isssued in International Application No. PCT/US2015/056467, dated Feb. 9, 2016 (13 Pages).
Morrison et al., "Combinatorial Alanine-Scanning", Current Opinion in Chemical Biology, vol. 5, pp. 302-307 (6 Pages).
Yang et al., "Mutational Analysis of Residues in the Nucleotide Binding Domain of Human Terminal Deoxynucleotidyl Transferase", Journal of Biological Chemistry, Apr. 22, 1994, pp. 11859-11868 (10 Pages).

* cited by examiner

*Primary Examiner* — Anand U Desai
(74) *Attorney, Agent, or Firm* — Brown Rudnick LLP; Thomas C. Meyers

(57) ABSTRACT

The invention includes methods for identifying polymerases, such as modified terminal nucleotidyl transferases (TdT), that are capable of binding nucleotides comprising removable 3'-O-blocking moieties to a nucleic acid initiator, without the use of a template. The invention further includes the identified polymerases, and methods of using the polymerases for de novo synthesis of predetermined oligonucleotide sequences.

27 Claims, 16 Drawing Sheets

Specification includes a Sequence Listing.

| Mutant (Crystal Numbering) | GGFRR | TGSR | 3'-AzM-dTTP | 3'-AzM-dATP | 3'-AzM-dGTP | 3'-Aminoxy-dTTP |
|---|---|---|---|---|---|---|
| E180D+W450H | N | N | + | ≤0 | ≤0 | + |
| M192E | N | N | + | + | n/a | + |
| E180K | N | N | + | + | + | + |
| E180K+R454A | N | Y | + | + | n/a | + |
| R454K | N | Y | + | + | n/a | + |
| M192K | N | N | + | + | + | + |
| M192K+E180K | N | N | + | + | + | + |
| Q455I | N | N | + | + | n/a | + |
| M192W | N | N | n/a | + | n/a | n/a |

| Mutant (Crystal Numbering) | GGFRR | TGSR | 3'-AzM-dATP | 3'-MOM-dTTP | 3'-MTM-dCTP |
|---|---|---|---|---|---|
| E180R | N | N | ≤0 | ≤0 | + |
| E180L | N | N | ≤0 | ≤0 | + |
| M192R | N | N | ≤0 | ≤0 | + |
| E180K+R454I | N | Y | ≤0 | ≤0 | + |
| E180D+M192E | N | N | ≤0 | ≤0 | + |
| E180D+M192E+R454T | N | Y | ≤0 | ≤0 | + |
| E180K+W450H | N | N | ≤0 | + | ≤0 |

| Mutant (Crystal Numbering) | GGFRR | TGSR | 3'-AzM-dTTP | 3'-AzM-dATP | 3'-AzM-dGTP | 3'-Aminoxy-dTTP | 3'-MOM-dTTP | 3'-MTM-dCTP | 3'-Aminoxy-dATP | 3'-Aminoxy-dGTP | 3'-Aminoxy-dCTP | 3'-O-methyl-dATP | 3'-O-methyl-dGTP | 3'-O-methyl-dCTP |
|---|---|---|---|---|---|---|---|---|---|---|---|---|---|---|
| N474R | N | N | ≤0 | + | n/a | + | ≤0 | ≤0 | + | + | + | + | + | ≤0 |
| R461V | N | N | + | ≤0 | n/a | + | + | + | + | + | + | + | + | + |

FIG. 5

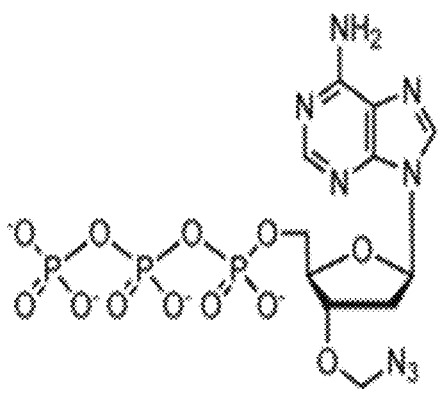
3'-O-N₃-dATP
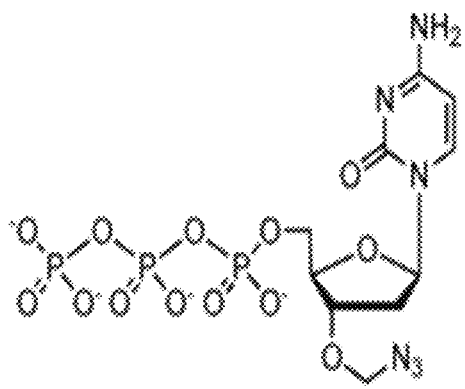
3'-O-N₃-dCTP
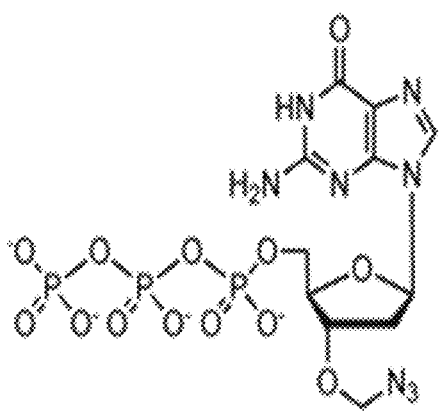
3'-O-N₃-dGTP
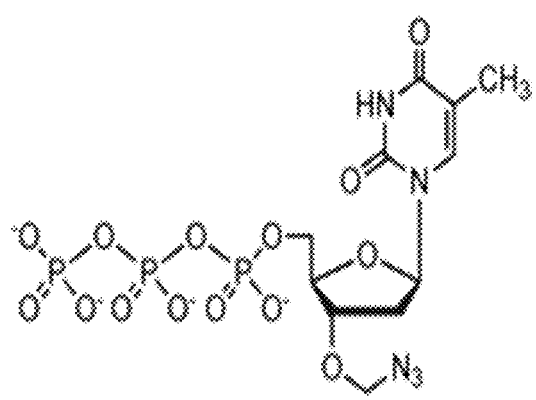
3'-O-N₃-dTTP
FIG. 6

```
                        SEQUENCE LISTING

<160> NUMBER OF SEQ ID NOS: 12

<210> SEQ ID NO 1
<211> LENGTH: 520
<212> TYPE: PRT
<213> ORGANISM: Bos taurus

<400> SEQUENCE: 1

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
        115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
```

```
                    260                 265                 270
Thr Ser Glu Lys Trp Phe Arg Met Gly Phe Arg Ser Leu Ser Lys Ile
                275                 280                 285
Met Ser Asp Lys Thr Leu Lys Phe Thr Lys Met Gln Lys Ala Gly Phe
            290                 295                 300
Leu Tyr Tyr Glu Asp Leu Val Ser Cys Val Thr Arg Ala Glu Ala Glu
305                 310                 315                 320
Ala Val Gly Val Leu Val Lys Glu Ala Val Trp Ala Phe Leu Pro Asp
                325                 330                 335
Ala Phe Val Thr Met Thr Gly Gly Phe Arg Arg Gly Lys Lys Ile Gly
                340                 345                 350
His Asp Val Asp Phe Leu Ile Thr Ser Pro Gly Ser Ala Glu Asp Glu
            355                 360                 365
Glu Gln Leu Leu Pro Lys Val Ile Asn Leu Trp Glu Lys Lys Gly Leu
        370                 375                 380
Leu Leu Tyr Tyr Asp Leu Val Glu Ser Thr Phe Glu Lys Phe Lys Leu
385                 390                 395                 400
Pro Ser Arg Gln Val Asp Thr Leu Asp His Phe Gln Lys Cys Phe Leu
                405                 410                 415
Ile Leu Lys Leu His His Gln Arg Val Asp Ser Ser Lys Ser Asn Gln
                420                 425                 430
Gln Glu Gly Lys Thr Trp Lys Ala Ile Arg Val Asp Leu Val Met Cys
            435                 440                 445
Pro Tyr Glu Asn Arg Ala Phe Ala Leu Leu Gly Trp Thr Gly Ser Arg
        450                 455                 460
Gln Phe Glu Arg Asp Ile Arg Arg Tyr Ala Thr His Glu Arg Lys Met
465                 470                 475                 480
Met Leu Asp Asn His Ala Leu Tyr Asp Lys Thr Lys Arg Val Phe Leu
                485                 490                 495
Lys Ala Glu Ser Glu Glu Glu Ile Phe Ala His Leu Gly Leu Asp Tyr
                500                 505                 510
Ile Glu Pro Trp Glu Arg Asn Ala
        515                 520

<210> SEQ ID NO 2
<211> LENGTH: 1923
<212> TYPE: DNA
<213> ORGANISM: Bos taurus

<400> SEQUENCE: 2
ctcttctgga gataccactt gatggcacag cagaggcagc atcagcgtct tcccatggat      60
ccgctgtgca cagcctcctc aggccctcgg aagaagagac caggcaggt gggtgcctca     120 atggcctccc ctcctcatga catcaagttt caaaatttgg tcctcttcat tttggagaag     180
aaaatgggaa ccacccgcag aaacttcctc atggagctgg ctcgaaggaa aggtttcagg     240
gttgaaaatg agctcagtga ttctgtcacc cacattgtag cagaaaacaa ctctggttca     300
gaggttctcg agtggcttca ggtacagaac ataagagcca gctcgcagct agaactcctt     360
gatgtctcct ggctgatcga agtatggga gcaggaaaac cagtggagat tacaggaaaa     420
caccagcttg ttgtgagaac agactattca gctaccccaa acccaggctt ccagaagact     480
ccaccacttg ctgtaaaaaa gatctcccag tacgcgtgtc aaagaaaaac cactttgaac     540
aactataacc acatattcac ggatgccttt gagatactgg ctgaaaattc tgagtttaaa     600
gaaaatgaag tctcttatgt gacatttatg agagcagctt ctgtacttaa atctctgcca     660
```

```
ttcacaatca tcagtatgaa ggatacagaa ggaattccct gcctggggga caaggtgaag      720
tgtatcatag aggaaattat tgaagatgga gaaagttctg aagttaaagc tgtgttaaat      780
gatgaacgat atcagtcctt caaactcttt acttctgttt ttggagtggg actgaagaca      840
tctgagaaat ggttcaggat ggggttcaga tctctgagta aaataatgtc agacaaaacc      900
ctgaaattca caaaaatgca gaaagcagga tttctctatt atgaagacct tgtcagctgc      960
gtgaccaggg ccgaagcaga ggcggttggc gtgctggtta agaggctgtg tgggcatttc     1020
tgccggatgc ctttgtcacc atgacagga ggattccgca ggggtaagaa gattgggcat     1080
gatgtagatt ttttaattac cagcccagga tcagcagagg atgaagagca acttttgcct     1140
aaagtgataa acttatggga aaaaaggga ttactttta attatgacct tgtggagtca     1200
acatttgaaa agttcaagtt gccaagcagg caggtggata cttagatca ttttcaaaaa     1260 tgctttctga ttttaaaatt gcaccatcag agagtagaca gtagcaagtc caaccagcag     1320
gaaggaaaga cctggaaggc catccgtgtg gacctggtta tgtgcccta cgagaaccgt     1380 gcctttgccc tgctaggctg gactggctcc cggcagtttg agagagacat ccggcgctat     1440
gccacacacg agcggaagat gatgctggat aaccacgctt tatatgacaa gaccaagagg     1500
gtatttctca agcggaaag tgaagaagaa atctttgcac atctgggatt ggactacatt     1560
gaaccatggg aaagaaatgc ttaggagaaa gctgtcaact ttttttcttt ctgttctttt     1620
tttcaggtta gacaaattat gcttcatatt ataatgaaag atgccttagt caagtttggg     1680
attctttaca ttttaccaag atgtagattg cttctagaaa taagtagttt tggaaacgtg     1740
atcaggcacc ccctgggtta tgctctggca agccatttgc aggactgatg tgtagaactc     1800
gcaatgcatt ttccatagaa acagtgttgg aattggtggc tcatttccag ggaagttcat     1860
caaagcccac tttgcccaca gtgtagctga atactgtat acttgccaat aaaaatagga     1920
aac                                                                   1923
```

<210> SEQ ID NO 3
<211> LENGTH: 392
<212> TYPE: PRT
<213> ORGANISM: Bos taurus

<400> SEQUENCE: 3

```
Met Arg Gly Ser His His His His His His Arg Thr Asp Tyr Ser Ala
1               5                   10                  15

Thr Pro Asn Pro Gly Phe Gln Lys Thr Pro Leu Ala Val Lys Lys
            20                  25                  30

Ile Ser Gln Tyr Ala Cys Gln Arg Lys Thr Thr Leu Asn Asn Tyr Asn
        35                  40                  45

His Ile Asp Ala Phe Glu Ile Leu Ala Glu Asn Ser Glu Phe Lys Glu
    50                  55                  60

Asn Glu Val Ser Tyr Val Thr Phe Met Arg Ala Ala Ser Val Leu Lys
65                  70                  75                  80

Ser Leu Pro Phe Thr Ile Ile Ser Met Lys Asp Thr Phe Thr Glu Gly
                85                  90                  95

Ile Pro Cys Leu Gly Asp Lys Val Lys Cys Ile Glu Glu Ile Ile
            100                 105                 110

Glu Asp Gly Glu Ser Ser Glu Val Lys Ala Val Leu Asn Asp Glu Arg
        115                 120                 125

Tyr Gln Ser Phe Lys Leu Ser Val Phe Gly Val Gly Leu Lys Thr Ser
    130                 135                 140
```

```
Glu Lys Trp Phe Arg Met Gly Phe Thr Phe Arg Ser Leu Ser Lys Ile
145                 150                 155                 160

Met Ser Asp Lys Thr Leu Lys Lys Met Gln Lys Ala Gly Phe Leu Tyr
                165                 170                 175

Tyr Glu Asp Leu Val Ser Cys Val Thr Arg Ala Glu Ala Glu Ala Val
            180                 185                 190

Gly Val Leu Val Lys Glu Ala Val Trp Ala Phe Leu Pro Asp Ala Phe
        195                 200                 205

Val Thr Met Thr Gly Gly Phe Arg Arg Gly Lys Lys Ile Gly His Asp
210                 215                 220

Val Asp Phe Leu Ile Thr Ser Pro Gly Ser Ala Glu Asp Glu Glu Gln
225                 230                 235                 240

Leu Leu Pro Lys Val Ile Asn Leu Trp Glu Lys Lys Gly Leu Leu Leu
                245                 250                 255

Tyr Tyr Asp Leu Val Glu Ser Thr Phe Glu Lys Phe Lys Phe Thr Leu
            260                 265                 270

Pro Ser Arg Gln Val Asp Thr Leu Asp His Phe Gln Lys Cys Phe Leu
        275                 280                 285

Ile Leu Lys Leu His His Gln Arg Val Asp Ser Ser Lys Ser Asn Gln
290                 295                 300

Gln Glu Gly Lys Thr Trp Lys Ala Ile Arg Val Asp Leu Val Met Cys
305                 310                 315                 320

Pro Tyr Glu Asn Arg Ala Phe Ala Leu Leu Gly Trp Thr Gly Ser Arg
                325                 330                 335

Gln Phe Glu Arg Asp Ile Arg Arg Tyr Ala Thr His Glu Arg Lys Met
            340                 345                 350

Met Leu Asp Asn His Ala Leu Tyr Asp Lys Thr Lys Arg Val Phe Leu
        355                 360                 365

Lys Ala Glu Ser Glu Glu Glu Ile Phe Ala His Leu Gly Leu Asp Tyr
            370                 375                 380

Ile Glu Pro Trp Glu Arg Asn Ala
385                 390

<210> SEQ ID NO 4
<211> LENGTH: 1187
<212> TYPE: DNA
<213> ORGANISM: Bos taurus

<400> SEQUENCE: 4
atgagaggat cgcatcacca tcaccatcac agaacagact attcagctac cccaaaccca      60
ggcttccaga agactccacc acttgctgta aaaagatct cccagtacgc gtgtcaaaga     120
aaaaccactt tgaacaacta taaccacata ttcacggatg cctttgagat actggctgaa     180
aattctgagt ttaaagaaaa tgaagtctct tatgtgacat ttatgagagc agcttctgta     240
cttaaatctc tgccattcac aatcatcagt atgaaggata cagaaggaat tccctgcctg     300
ggggacaagg tgaagtgtat catagaggaa attattgaag atggagaaag ttctgaagtt     360
aaagctgtgt taaatgatga acgatatcag tccttcaaac tctttacttc tgttttttgga     420 gtgggactga agacatctga gaatggttc aggatggggt tcagatctct gagtaaaata     480
atgtcagaca aaaccctgaa attcacaaaa atgcagaaag caggatttct ctattatgaa     540
gaccttgtca gctgcgtgac cagggccgaa gcagaggcgg ttggcgtgct ggttaaagag     600
gctgtgtggg catttctgcc ggatgccttt gtcaccatga caggaggatt ccgcaggggt     660
```

```
aagaagattg ggcatgatgt agattttta attaccagcc caggatcagc agaggatgaa    720
gagcaacttt tgcctaaagt gataaactta tgggaaaaaa agggattact tttatattat    780
gaccttgtgg agtcaacatt tgaaaagttc aagttgccaa gcaggcaggt ggatacttta    840
gatcattttc aaaaatgctt tctgatttta aaattgcacc atcagagagt agacagtagc    900
aagtccaacc agcaggaagg aaagacctgg aaggccatcc gtgtggacct ggttatgtgc    960
ccctacgaga accgtgcctt tgccctgcta ggctggactg ctcccggca gtttgagaga   1020 gacatccggc gctatgccac acgagcggg aagatgatgc tggataacca cgctttatat   1080
gacaagacca agagggtatt tctcaaagcg gaaagtgaag aagaaatctt tgcacatctg   1140
ggattggact acattgaacc atgggaaaga atgcttaag cttgcgc                 1187
```

<210> SEQ ID NO 5
<211> LENGTH: 379
<212> TYPE: PRT
<213> ORGANISM: Bos taurus

<400> SEQUENCE: 5

```
Met Arg Gly Ser His His His His His Lys Thr Pro Pro Leu Ala
1               5                   10                  15

Val Lys Lys Ile Ser Gln Tyr Ala Cys Gln Arg Lys Thr Thr Leu Asn
            20                  25                  30

Asn Tyr Asn His Ile Asp Ala Phe Glu Ile Leu Ala Glu Asn Ser Glu
        35                  40                  45

Phe Lys Glu Asn Glu Val Ser Tyr Val Thr Phe Met Arg Ala Ala Ser
    50                  55                  60

Val Leu Lys Ser Leu Pro Phe Thr Ile Ile Ser Met Lys Asp Thr Phe
65                  70                  75                  80

Thr Glu Gly Ile Pro Cys Leu Gly Asp Lys Val Lys Cys Ile Ile Glu
                85                  90                  95

Glu Ile Ile Glu Asp Gly Glu Ser Ser Glu Val Lys Ala Val Leu Asn
            100                 105                 110

Asp Glu Arg Tyr Gln Ser Phe Lys Leu Ser Val Phe Gly Val Gly Leu
        115                 120                 125

Lys Thr Ser Glu Lys Trp Phe Arg Met Gly Phe Thr Phe Arg Ser Leu
    130                 135                 140

Ser Lys Ile Met Ser Asp Lys Thr Leu Lys Met Gln Lys Ala Gly
145                 150                 155                 160

Phe Leu Tyr Tyr Glu Asp Leu Val Ser Cys Val Thr Arg Ala Glu Ala
                165                 170                 175

Glu Ala Val Gly Val Leu Val Lys Glu Ala Val Trp Ala Phe Leu Pro
            180                 185                 190

Asp Ala Phe Val Thr Met Thr Gly Gly Phe Arg Arg Gly Lys Lys Ile
        195                 200                 205

Gly His Asp Val Asp Phe Leu Ile Thr Ser Pro Gly Ser Ala Glu Asp
    210                 215                 220

Glu Glu Gln Leu Leu Pro Lys Val Ile Asn Leu Trp Glu Lys Lys Gly
225                 230                 235                 240

Leu Leu Leu Tyr Tyr Asp Leu Val Glu Ser Thr Phe Glu Lys Phe Lys
                245                 250                 255

Phe Thr Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
        275                 280                 285
```

Ser Asn Gln Gln Glu Gly Lys Thr Trp Lys Ala Ile Arg Val Asp Leu
        290                 295                 300

Val Met Cys Pro Tyr Glu Asn Arg Ala Phe Ala Leu Leu Gly Trp Thr
305                 310                 315                 320

Gly Ser Arg Gln Phe Glu Arg Asp Ile Arg Tyr Ala Thr His Glu
                325                 330                 335

Arg Lys Met Met Leu Asp Asn His Ala Leu Tyr Asp Lys Thr Lys Arg
                340                 345                 350

Val Phe Leu Lys Ala Glu Ser Glu Glu Ile Phe Ala His Leu Gly
            355                 360                 365

Leu Asp Tyr Ile Glu Pro Trp Glu Arg Asn Ala
        370                 375

<210> SEQ ID NO 6
<211> LENGTH: 1148
<212> TYPE: DNA
<213> ORGANISM: Bos taurus

<400> SEQUENCE: 6
atgagaggat cgcatcacca tcaccatcac aagactccac cacttgctgt aaaaaagatc      60
tcccagtacg cgtgtcaaag aaaaaccact ttgaacaact ataaccacat attcacggat     120
gcctttgaga tactggctga aaattctgag tttaaagaaa atgaagtctc ttatgtgaca     180
tttatgagag cagcttctgt acttaaatct ctgccattca caatcatcag tatgaaggat     240
acagaaggaa ttccctgcct ggggacaag gtgaagtgta tcatagagga aattattgaa     300
gatggagaaa gttctgaagt taaagctgtg ttaaatgatg aacgatatca gtccttcaaa     360
ctctttactt ctgttttgg agtgggactg aagacatctg agaaatggtt caggatgggg     420
ttcagatctc tgagtaaaat aatgtcagac aaaaccctga attcacaaa atgcagaaa      480 gcaggatttc tctattatga agaccttgtc agctgcgtga ccagggccga agcagaggcg     540
gttggcgtgc tggttaaaga ggctgtgtgg gcatttctgc cggatgcctt tgtcaccatg     600
acaggaggat ccgcaggggt aagaagatt gggcatgatg tagattttt aattaccagc     660 ccaggatcag cagaggatga agagcaactt ttgcctaaag tgataaactt atgggaaaaa     720
aagggattac ttttatatta tgaccttgtg gagtcaacat ttgaaaagtt caagttgcca     780
agcaggcagg tggatacttt agatcatttt caaaaatgct ttctgatttt aaaattgcac     840
catcagagag tagacagtag caagtccaac cagcaggaag aaagacctg gaaggccatc      900 cgtgtggacc tggttatgtg ccctacgag aaccgtgcct tgccctgct aggctggact     960 ggctcccggc agtttgagag agacatccgg cgctatgcca cacacgagcg aagatgatg    1020 ctggataacc acgctttata tgacaagacc aagagggtat ttctcaaagc ggaaagtgaa    1080
gaagaaatct ttgcacatct gggattggac tacattgaac catgggaaag aaatgcttaa    1140
gcttgcgc                                                            1148

<210> SEQ ID NO 7
<211> LENGTH: 370
<212> TYPE: PRT
<213> ORGANISM: Bos taurus

<400> SEQUENCE: 7

Met Arg Gly Ser His His His His His His Ile Ser Gln Tyr Ala Cys
1               5                   10                  15

Gln Arg Lys Thr Thr Leu Asn Asn Tyr Asn His Ile Asp Ala Phe Glu

```
            20                  25                  30
Ile Leu Ala Glu Asn Ser Glu Phe Lys Glu Asn Glu Val Ser Tyr Val
         35                  40                  45

Thr Phe Met Arg Ala Ala Ser Val Leu Lys Ser Leu Pro Phe Thr Ile
 50                  55                  60

Ile Ser Met Lys Asp Thr Phe Thr Glu Gly Ile Pro Cys Leu Gly Asp
 65                  70                  75                  80

Lys Val Lys Cys Ile Ile Glu Glu Ile Ile Glu Asp Gly Glu Ser Ser
                 85                  90                  95

Glu Val Lys Ala Val Leu Asn Asp Glu Arg Tyr Gln Ser Phe Lys Leu
            100                 105                 110

Ser Val Phe Gly Val Gly Leu Lys Thr Ser Glu Lys Trp Phe Arg Met
        115                 120                 125

Gly Phe Thr Phe Arg Ser Leu Ser Lys Ile Met Ser Asp Lys Thr Leu
    130                 135                 140

Lys Lys Met Gln Lys Ala Gly Phe Leu Tyr Tyr Glu Asp Leu Val Ser
145                 150                 155                 160

Cys Val Thr Arg Ala Glu Ala Glu Ala Val Gly Val Leu Val Lys Glu
                165                 170                 175

Ala Val Trp Ala Phe Leu Pro Asp Ala Phe Val Thr Met Thr Gly Gly
            180                 185                 190

Phe Arg Arg Gly Lys Lys Ile Gly His Asp Val Asp Phe Leu Ile Thr
        195                 200                 205

Ser Pro Gly Ser Ala Glu Asp Glu Glu Gln Leu Leu Pro Lys Val Ile
    210                 215                 220

Asn Leu Trp Glu Lys Lys Gly Leu Leu Leu Tyr Tyr Asp Leu Val Glu
225                 230                 235                 240

Ser Thr Phe Glu Lys Phe Lys Phe Thr Leu Pro Ser Arg Gln Val Asp
                245                 250                 255

Thr Leu Asp His Phe Gln Lys Cys Phe Leu Ile Leu Lys Leu His His
            260                 265                 270

Gln Arg Val Asp Ser Ser Lys Ser Asn Gln Gln Glu Gly Lys Thr Trp
        275                 280                 285

Lys Ala Ile Arg Val Asp Leu Val Met Cys Pro Tyr Glu Asn Arg Ala
    290                 295                 300

Phe Ala Leu Leu Gly Trp Thr Gly Ser Arg Gln Phe Glu Arg Asp Ile
305                 310                 315                 320

Arg Arg Tyr Ala Thr His Glu Arg Lys Met Met Leu Asp Asn His Ala
                325                 330                 335

Leu Tyr Asp Lys Thr Lys Arg Val Phe Leu Lys Ala Glu Ser Glu Glu
            340                 345                 350

Glu Ile Phe Ala His Leu Gly Leu Asp Tyr Ile Glu Pro Trp Glu Arg
        355                 360                 365

Asn Ala
    370

<210> SEQ ID NO 8
<211> LENGTH: 1121
<212> TYPE: DNA
<213> ORGANISM: Bos taurus

<400> SEQUENCE: 8
atgagaggat cgcatcacca tcaccatcac atctcccagt acgcgtgtca agaaaaacc      60 actttgaaca actataacca catattcacg gatgcctttg agatactggc tgaaaattct    120
```

```
gagtttaaag aaaatgaagt ctcttatgtg acatttatga gagcagcttc tgtacttaaa      180
tctctgccat tcacaatcat cagtatgaag gatacagaag gaattccctg cctgggggac      240
aaggtgaagt gtatcataga ggaaattatt gaagatggag aaagttctga agttaaagct      300
gtgttaaatg atgaacgata tcagtccttc aaactcttta cttctgtttt tggagtggga      360
ctgaagacat ctgagaaatg gttcaggatg gggttcagat ctctgagtaa aataatgtca      420
gacaaaaccc tgaaattcac aaaaatgcag aaagcaggat ttctctatta tgaagacctt      480
gtcagctgcg tgaccagggc cgaagcagag gcggttggcg tgctggttaa agaggctgtg      540
tgggcatttc tgccggatgc ctttgtcacc atgacaggag gattccgcag gggtaagaag      600
attgggcatg atgtagattt tttaattacc agcccaggat cagcagagga tgaagagcaa      660
cttttgccta aagtgataaa cttatgggaa aaaagggat tactttttata ttatgacctt      720
gtggagtcaa catttgaaaa gttcaagttg ccaagcaggc aggtggatac tttagatcat      780
tttcaaaaat gctttctgat tttaaaattg caccatcaga gagtagacag tagcaagtcc      840
aaccagcagg aaggaaagac ctggaaggcc atccgtgtgg acctggttat gtgcccctac      900
gagaaccgtg cctttgccct gctaggctgg actggctccc ggcagtttga gagagacatc      960
cggcgctatg ccacacacga gcggaagatg atgctggata ccacgctttt atatgacaag     1020
accaagaggg tatttctcaa agcggaaagt gaagaagaaa tctttgcaca tctgggattg     1080
gactacattg aaccatggga agaaatgct taagcttgcg c                          1121
```

<210> SEQ ID NO 9
<211> LENGTH: 510
<212> TYPE: PRT
<213> ORGANISM: Mus musculus

<400> SEQUENCE: 9

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190
```

```
Arg Ala Ser Ser Val Leu Lys Ser Leu Pro Phe Pro Ile Thr Ser Met
            195                 200                 205

Lys Asp Thr Glu Gly Ile Pro Cys Leu Gly Asp Lys Val Lys Ser Ile
210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
            245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
            275                 280                 285

Gln Lys Ala Gly Phe Leu Tyr Tyr Glu Asp Leu Val Ser Cys Val Asn
290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
            355                 360                 365

Trp Lys Gln Gln Gly Leu Leu Leu Tyr Cys Asp Ile Leu Glu Ser Thr
370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 10
<211> LENGTH: 402
<212> TYPE: PRT
<213> ORGANISM: Mus musculus

<400> SEQUENCE: 10

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Leu Glu Lys Lys Ile Ser Gln Tyr Ala Cys Gln
            35                  40                  45

Arg Arg Thr Thr Leu Asn Asn Tyr Asn Gln Leu Phe Thr Asp Ala Leu
50                  55                  60
```

```
Asp Ile Leu Ala Glu Asn Asp Glu Leu Arg Glu Asn Glu Gly Ser Cys
 65                  70                  75                  80

Leu Ala Phe Met Arg Ala Ser Ser Val Leu Lys Ser Leu Pro Phe Pro
                 85                  90                  95

Ile Thr Ser Met Lys Asp Thr Glu Gly Ile Pro Cys Leu Gly Asp Lys
                100                 105                 110

Val Lys Ser Ile Ile Glu Gly Ile Glu Asp Gly Glu Ser Ser Glu
            115                 120                 125

Ala Lys Ala Val Leu Asn Asp Glu Arg Tyr Lys Ser Phe Lys Leu Phe
            130                 135                 140

Thr Ser Val Phe Gly Val Gly Leu Lys Thr Ala Glu Lys Trp Phe Arg
145                 150                 155                 160

Met Gly Phe Arg Thr Leu Ser Lys Ile Gln Ser Asp Lys Ser Leu Arg
                165                 170                 175

Phe Thr Gln Met Gln Lys Ala Gly Phe Leu Tyr Tyr Glu Asp Leu Val
                180                 185                 190

Ser Cys Val Asn Arg Pro Glu Ala Glu Ala Val Ser Met Leu Val Lys
            195                 200                 205

Glu Ala Val Val Thr Phe Leu Pro Asp Ala Leu Val Thr Met Thr Gly
210                 215                 220

Gly Phe Arg Arg Gly Lys Met Thr Gly His Asp Val Asp Phe Leu Ile
225                 230                 235                 240

Thr Ser Pro Glu Ala Thr Glu Asp Glu Glu Gln Gln Leu Leu His Lys
                245                 250                 255

Val Thr Asp Phe Trp Lys Gln Gln Gly Leu Leu Leu Tyr Cys Asp Ile
            260                 265                 270

Leu Glu Ser Thr Phe Glu Lys Phe Lys Gln Pro Ser Arg Lys Val Asp
            275                 280                 285

Ala Leu Asp His Phe Gln Lys Cys Phe Leu Ile Leu Lys Leu Asp His
290                 295                 300

Gly Arg Val His Ser Glu Lys Ser Gly Gln Gln Glu Gly Lys Gly Trp
305                 310                 315                 320

Lys Ala Ile Arg Val Asp Leu Val Met Cys Pro Tyr Asp Arg Arg Ala
                325                 330                 335

Phe Ala Leu Leu Gly Trp Thr Gly Ser Arg Gln Phe Glu Arg Asp Leu
                340                 345                 350

Arg Arg Tyr Ala Thr His Glu Arg Lys Met Met Leu Asp Asn His Ala
            355                 360                 365

Leu Tyr Asp Arg Thr Lys Arg Val Phe Leu Glu Ala Glu Ser Glu Glu
            370                 375                 380

Glu Ile Phe Ala His Leu Gly Leu Asp Tyr Ile Glu Pro Trp Glu Arg
385                 390                 395                 400

Asn Ala

<210> SEQ ID NO 11
<211> LENGTH: 409
<212> TYPE: PRT
<213> ORGANISM: Mus musculus

<400> SEQUENCE: 11

Met Arg Gly Ser His His His His His His Gly Met Ala Ser Met Thr
  1               5                  10                  15

Gly Gly Gln Gln Met Gly Arg Glu Asn Leu Tyr Phe Gln Gly Ser Pro
                 20                  25                  30
```

```
Ser Pro Val Pro Gly Ser Gln Asn Val Pro Ala Pro Ala Val Lys Lys
        35                  40                  45

Ile Ser Gln Tyr Ala Cys Gln Arg Thr Thr Leu Asn Asn Tyr Asn
50                  55                  60

Gln Leu Phe Thr Asp Ala Leu Asp Ile Leu Ala Glu Asn Asp Glu Leu
65                  70                  75                  80

Arg Glu Asn Glu Gly Ser Cys Leu Ala Phe Met Arg Ala Ser Ser Val
                85                  90                  95

Leu Lys Ser Leu Pro Phe Pro Ile Thr Ser Met Lys Asp Thr Glu Gly
            100                 105                 110

Ile Pro Cys Leu Gly Asp Lys Val Lys Ser Ile Glu Gly Ile Ile
            115                 120                 125

Glu Asp Gly Glu Ser Ser Glu Ala Lys Ala Val Leu Asn Asp Glu Arg
130                 135                 140

Tyr Lys Ser Phe Lys Leu Phe Thr Ser Val Phe Gly Val Gly Leu Lys
145                 150                 155                 160

Thr Ala Glu Lys Trp Phe Arg Met Gly Phe Arg Thr Leu Ser Lys Ile
                165                 170                 175

Gln Ser Asp Lys Ser Leu Arg Phe Thr Gln Met Gln Lys Ala Gly Phe
            180                 185                 190

Leu Tyr Tyr Glu Asp Leu Val Ser Cys Val Asn Arg Pro Glu Ala Glu
            195                 200                 205

Ala Val Ser Met Leu Val Lys Glu Ala Val Val Thr Phe Leu Pro Asp
210                 215                 220

Ala Leu Val Thr Met Thr Gly Gly Phe Arg Arg Gly Lys Met Thr Gly
225                 230                 235                 240

His Asp Val Asp Phe Leu Ile Thr Ser Pro Glu Ala Thr Glu Asp Glu
                245                 250                 255

Glu Gln Gln Leu Leu His Lys Val Thr Asp Phe Trp Lys Gln Gln Gly
            260                 265                 270

Leu Leu Leu Tyr Cys Asp Ile Leu Glu Ser Thr Phe Glu Lys Phe Lys
            275                 280                 285

Gln Pro Ser Arg Lys Val Asp Ala Leu Asp His Phe Gln Lys Cys Phe
290                 295                 300

Leu Ile Leu Lys Leu Asp His Gly Arg Val His Ser Glu Lys Ser Gly
305                 310                 315                 320

Gln Gln Glu Gly Lys Gly Trp Lys Ala Ile Arg Val Asp Leu Val Met
                325                 330                 335

Cys Pro Tyr Asp Arg Arg Ala Phe Ala Leu Leu Gly Trp Thr Gly Ser
            340                 345                 350

Arg Gln Phe Glu Arg Asp Leu Arg Arg Tyr Ala Thr His Glu Arg Lys
            355                 360                 365

Met Met Leu Asp Asn His Ala Leu Tyr Asp Arg Thr Lys Arg Val Phe
370                 375                 380

Leu Glu Ala Glu Ser Glu Glu Ile Phe Ala His Leu Gly Leu Asp
385                 390                 395                 400

Tyr Ile Glu Pro Trp Glu Arg Asn Ala
                405

<210> SEQ ID NO 12
<211> LENGTH: 42
<212> TYPE: DNA
<213> ORGANISM: Artificial Sequence
<220> FEATURE:
```

```
<223> OTHER INFORMATION: Synthesized

<400> SEQUENCE: 12
taataataat aataataata ataataataa taataatttt tt                    42
```

MODIFIED TEMPLATE-INDEPENDENT ENZYMES FOR POLYDEOXYNUCLEOTIDE SYNTHESIS

RELATED APPLICATIONS

This application is a continuation-in-part of U.S. Non-Provisional application Ser. No. 16/165,465, filed Oct. 19, 2018, which is a continuation-in-part of U.S. Non-Provisional application Ser. No. 16/113,757, filed Aug. 27, 2018, which is a continuation of U.S. Non-Provisional application Ser. No. 14/918,212, filed Oct. 20, 2015, now issued as U.S. Pat. No. 10,059,929, which claims priority to and the benefit of U.S. Provisional Application Ser. No. 62/065,976, filed Oct. 20, 2014, the content of each of which is incorporated by reference herein.

FIELD OF THE INVENTION

The invention relates to modified enzymes for de novo synthesis of polynucleotides with a desired sequence, and without the use of a template. As such, the invention provides the capability to make libraries of polynucleotides of varying sequence and varying length for research, genetic engineering, and gene therapy.

BACKGROUND

Most de novo nucleic acid sequences are synthesized using solid phase phosphoramidite-techniques developed more than 30 years ago. The technique involves the sequential de-protection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligo production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., *Nucleic Acids Res.*, vol. 38(8), p. 2522-2540, (2010), incorporated by reference herein in its entirety). Thus, there is a need for more efficient and cost-effective methods for oligonucleotide synthesis.

SUMMARY

The invention discloses modified terminal deoxynucleotidyl transferase (TdT) enzymes that can be used for de novo synthesis of oligonucleotides in the absence of a template. Methods for creating a template-independent polymerase through a combination of computational guidance and saturation mutagenesis, with a subsequent screen to identify functional mutants, are also disclosed. Native TdT enzymes are either inefficient or completely unable to incorporate the different blocked nucleotide analogs used in template-independent synthesis schemes. The present invention provides various TdT modifications that expand the enzyme's functionality with respect to blocked nucleotide analogs, especially those with 3'-O blocking groups. In particular, modified TdTs of the invention can be used to incorporate 3'-O-Phosphate-blocked nucleotide analogs where wild type TdTs may be unable to do so.

Methods of the invention include nucleic acid synthesis using 3'-O-blocked nucleotide analogs and Shrimp Alkaline Phosphatase (SAP) for controlled addition of selected nucleotides.

Using enzymes and methods of the invention, it will be possible to synthesize de novo polynucleotides faster and more cheaply. As such, the invention dramatically reduces the overall cost of synthesizing custom nucleic acids. In particular, the methods can be used to create template-independent transferases that can synthesize custom oligos in a stepwise fashion using modified 3' hydroxyl-blocked nucleotides. Because of the terminating group, synthesis pauses with the addition of each new base, whereupon the terminating group is cleaved, leaving a polynucleotide that is essentially identical to a naturally occurring nucleotide (i.e., is recognized by the enzyme as a substrate for further nucleotide incorporation).

The methods and enzymes of the invention represent an important step forward in synthetic biology because the enzymes will allow for aqueous phase, template-independent oligonucleotide synthesis. Such methods represent an improvement over the prior art in that they will greatly reduce the chemical waste produced during oligonucleotide synthesis while allowing for the production of longer polynucleotides. Furthermore, because the methods replace a chemical process with a biological one, costs will be reduced, and the complexity of automated synthetic systems will also be reduced. In an embodiment, a simple five-reagent delivery system can be used to build oligonucleotides in a stepwise fashion and will enable recycling of unused reagents.

Shown are the residues, that are in close proximity to the incoming dNTP and the targets of mutagenesis and screening.

FIG. 5 shows a table of TdT variants that were selected for increased incorporation of selected 3'-O-blocked dNTP analogs as described herein.

FIG. 6 shows exemplary 3'-O-azidomethyl deoxynucleotides that can be used to synthesize custom DNA oligomers using modified TdTs, as described herein.

Figure 7:
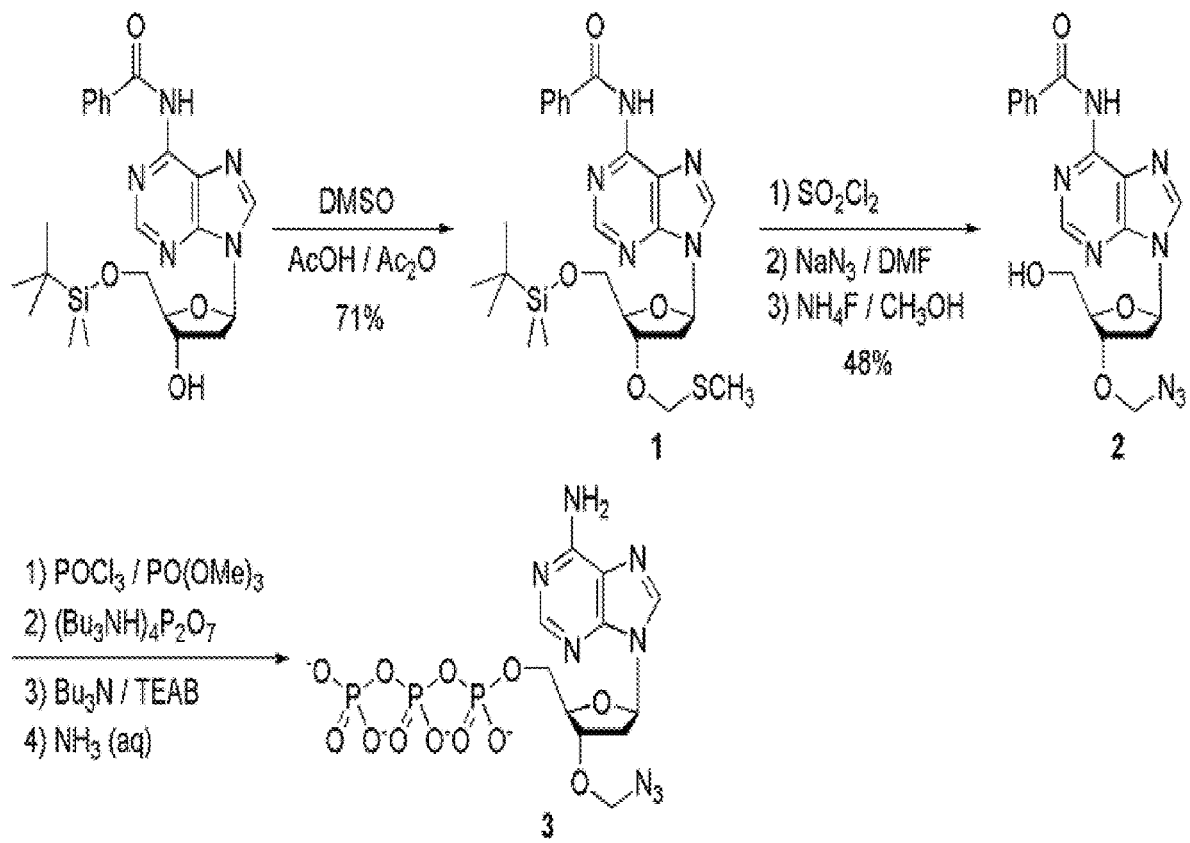

FIG. 7 shows a synthetic scheme for producing 3'-O-azidomethyl deoxyadenosine triphosphate (3'-O-azidomethyl-dATP).

Figure 8:
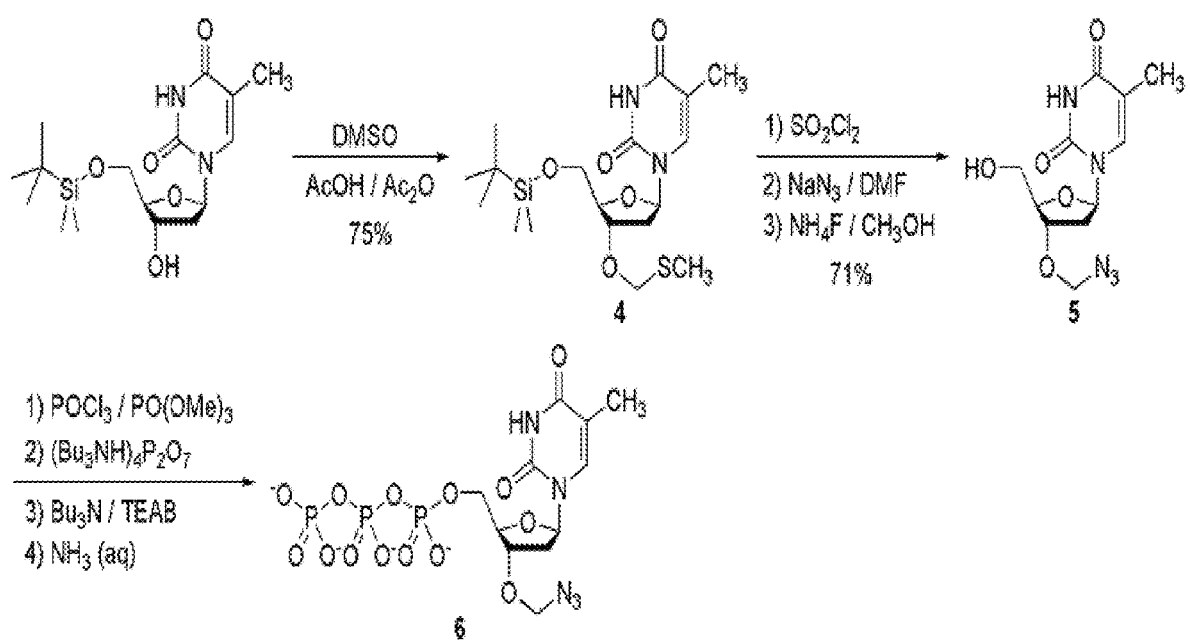

FIG. 8 shows a synthetic scheme for producing 3'-O-azidomethyl deoxythymidine triphosphate (3'-O-azidomethyl-dTTP).

Figure 9:
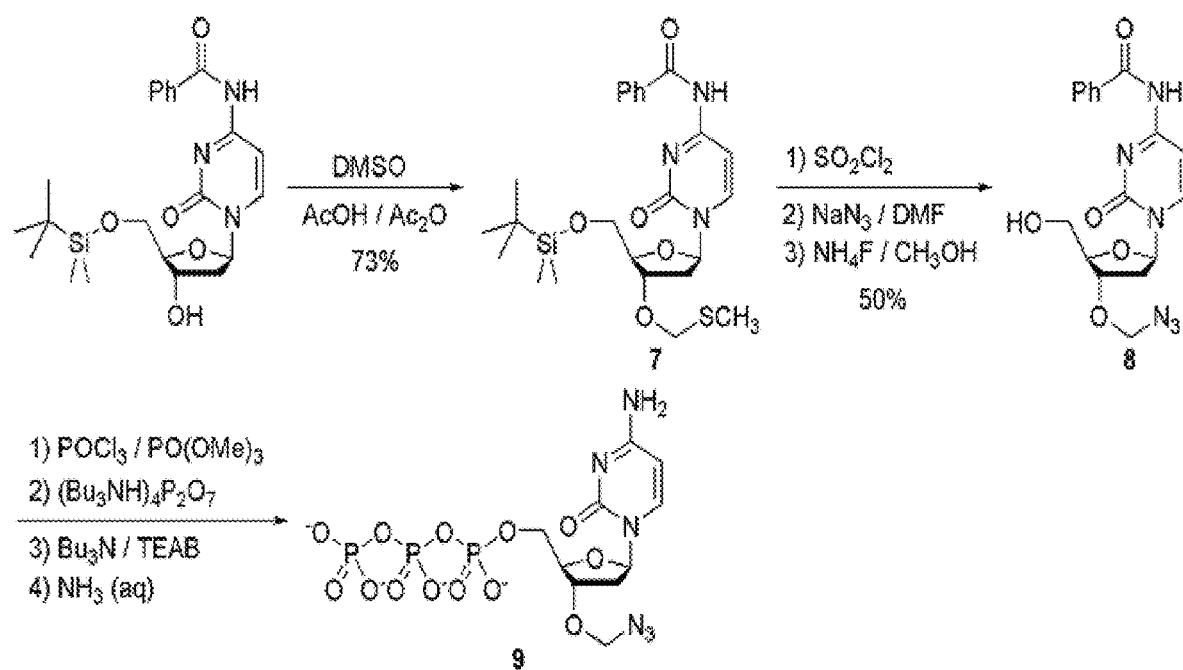

FIG. 9 shows a synthetic scheme for producing 3'-O-azidomethyl deoxycytidine triphosphate (3'-O-azidomethyl-dCTP).

Figure 10:
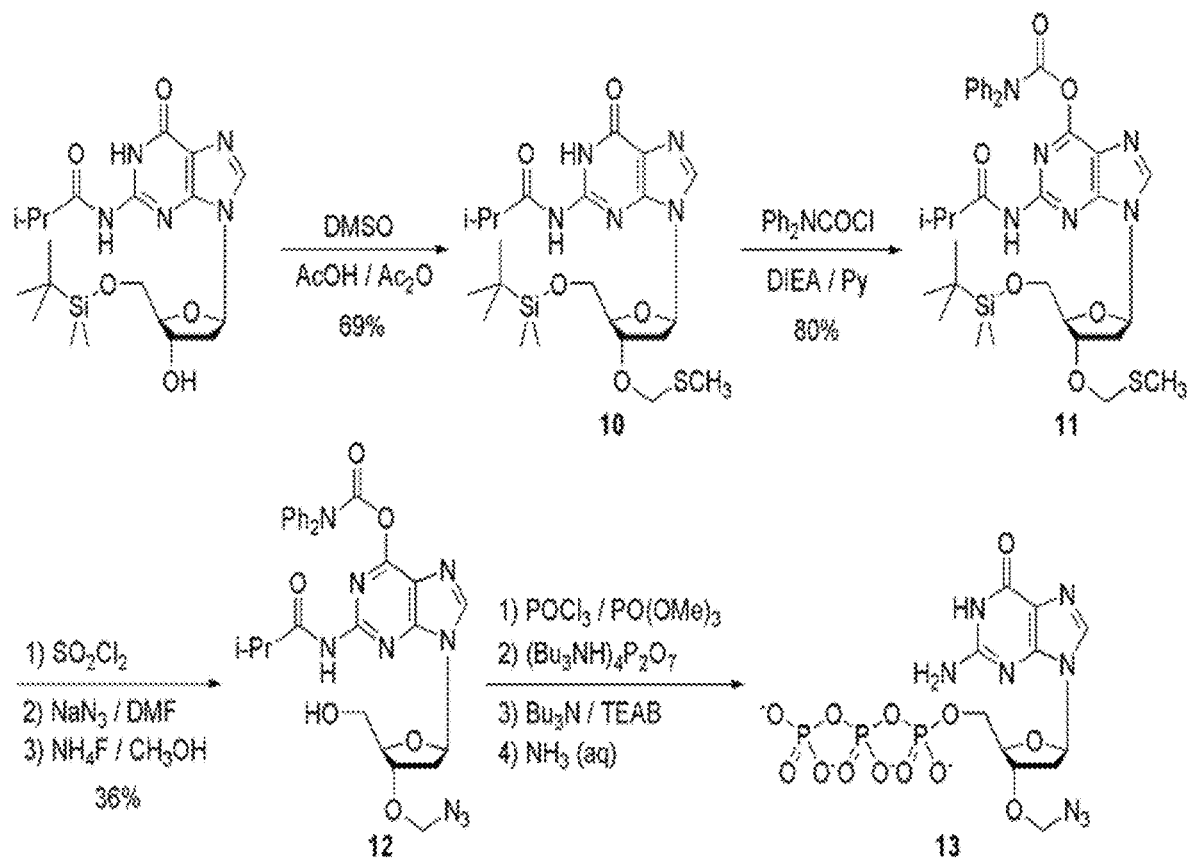

FIG. 10 shows a synthetic scheme for producing 3'-O-azidomethyl deoxyguanosine triphosphate (3'-O-azidomethyl-dGTP).

Figure 11:
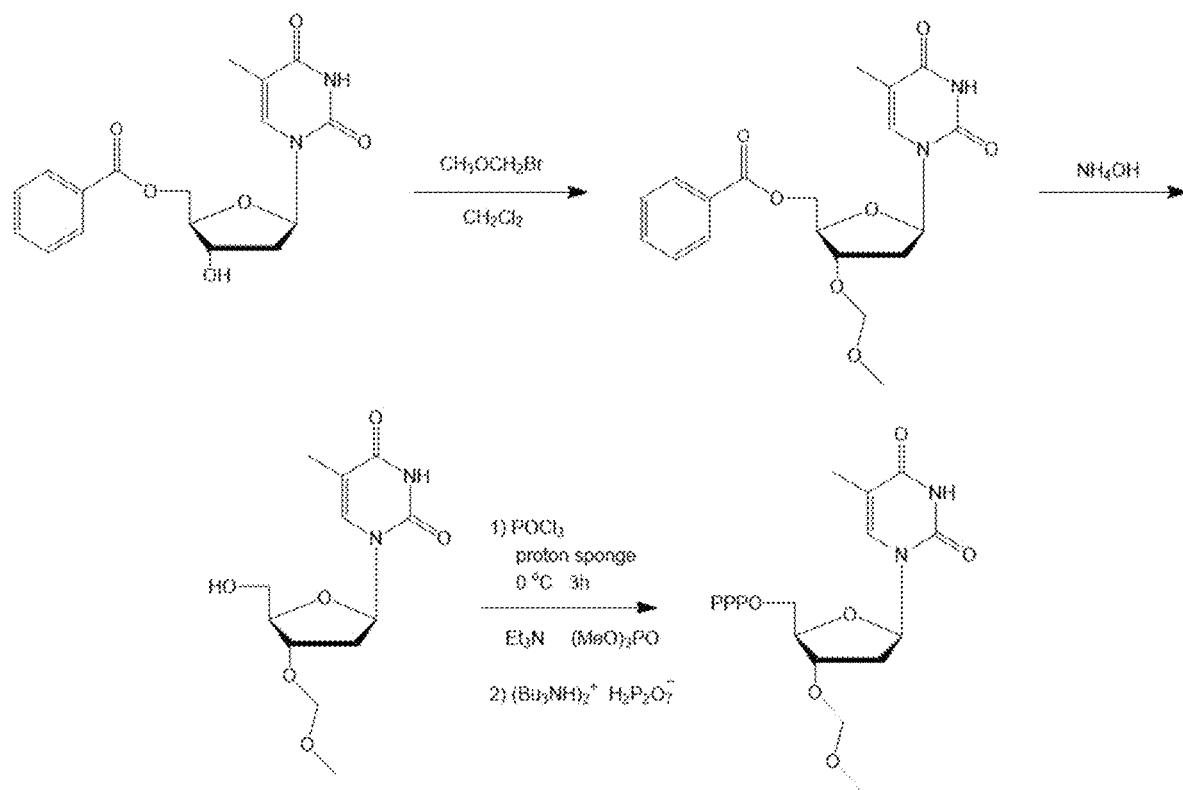

FIG. 11 shows a synthetic scheme for producing 3'-O-methoxymethyl deoxythymidine triphosphate (3'-O-MOM-dTTP).

Figure 12:
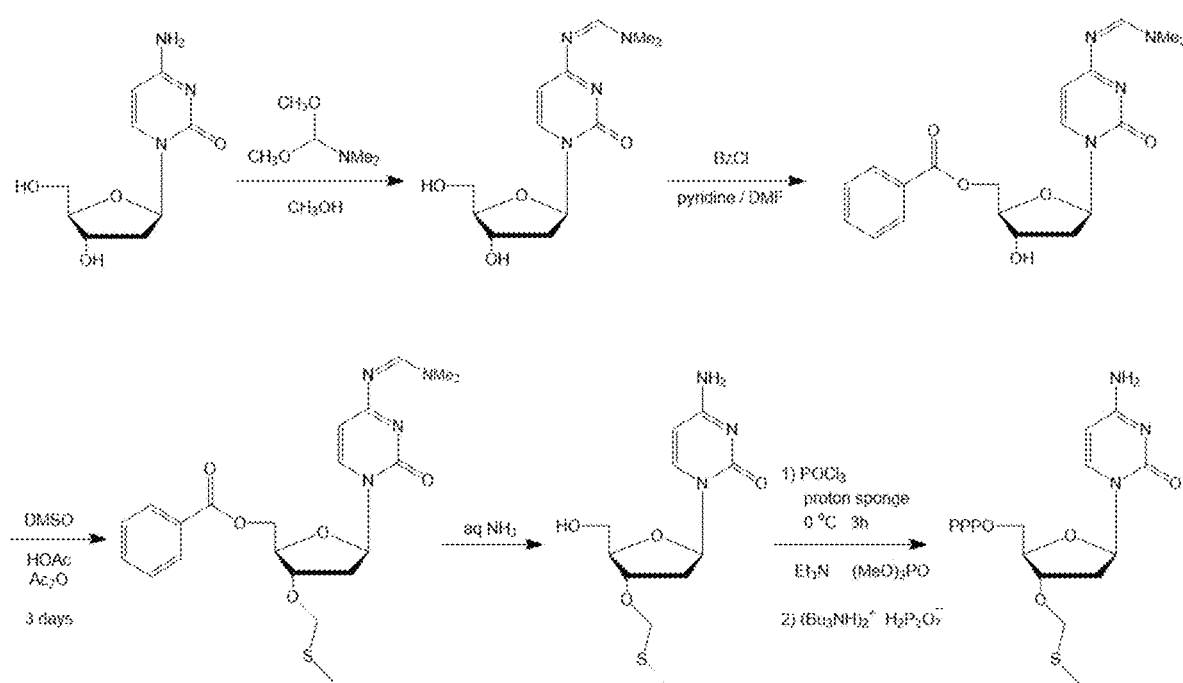

FIG. 12 shows a synthetic scheme for producing 3'-O-thiomethyl deoxycytidine triphosphate (3'-O-MTM-dCTP).

Figure 13:
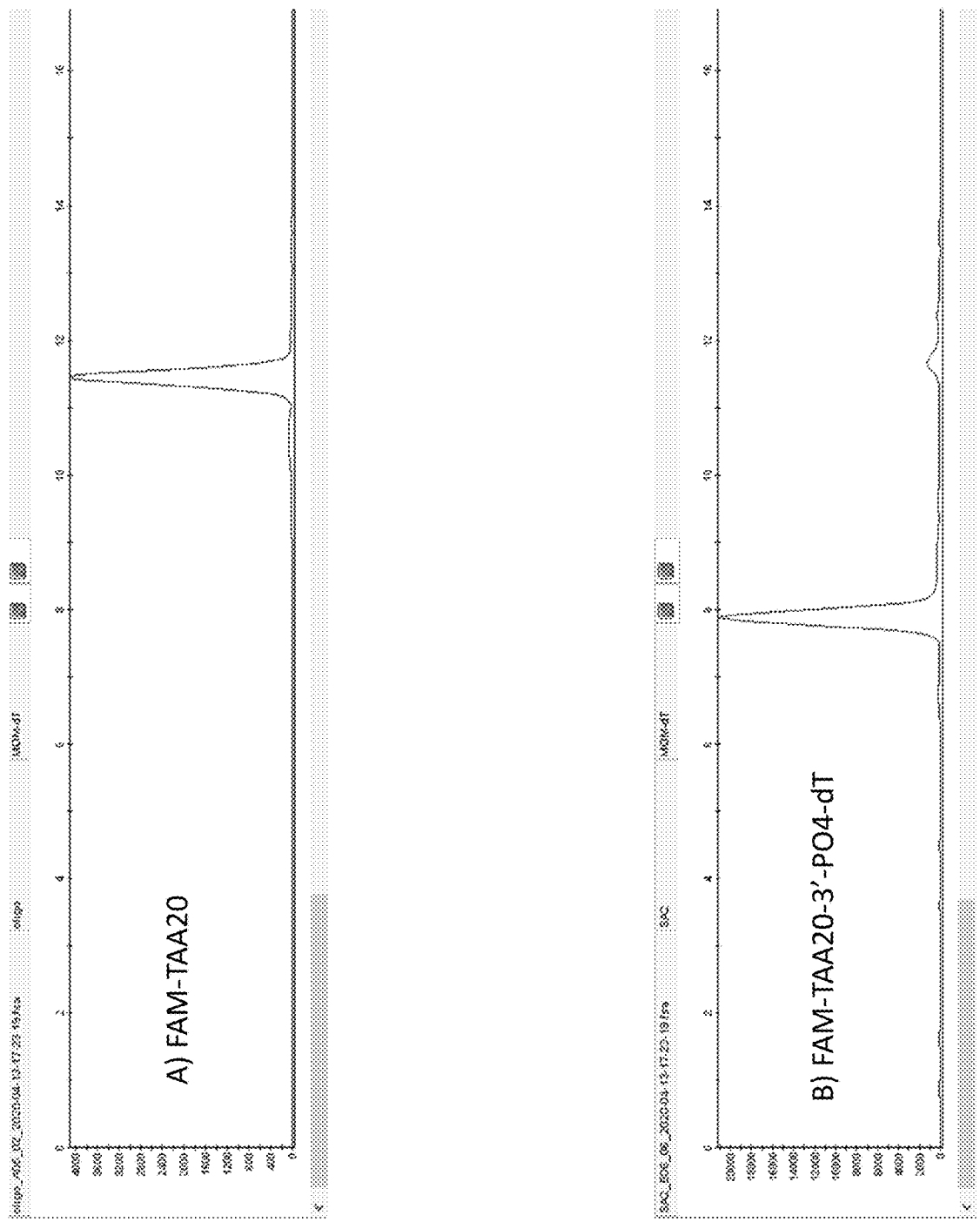

FIG. 13 shows CGE (Capillary Gel Electrophoresis) traces showing migration of chemically synthesized authentic standard of A) 5'-FAM-TAATAATAATAATAATTTTT compared to chemically synthesized authentic standard of B) 5'-FAM-TAATAATAATAATAATTTTT-PO4-3'.

Figure 14:
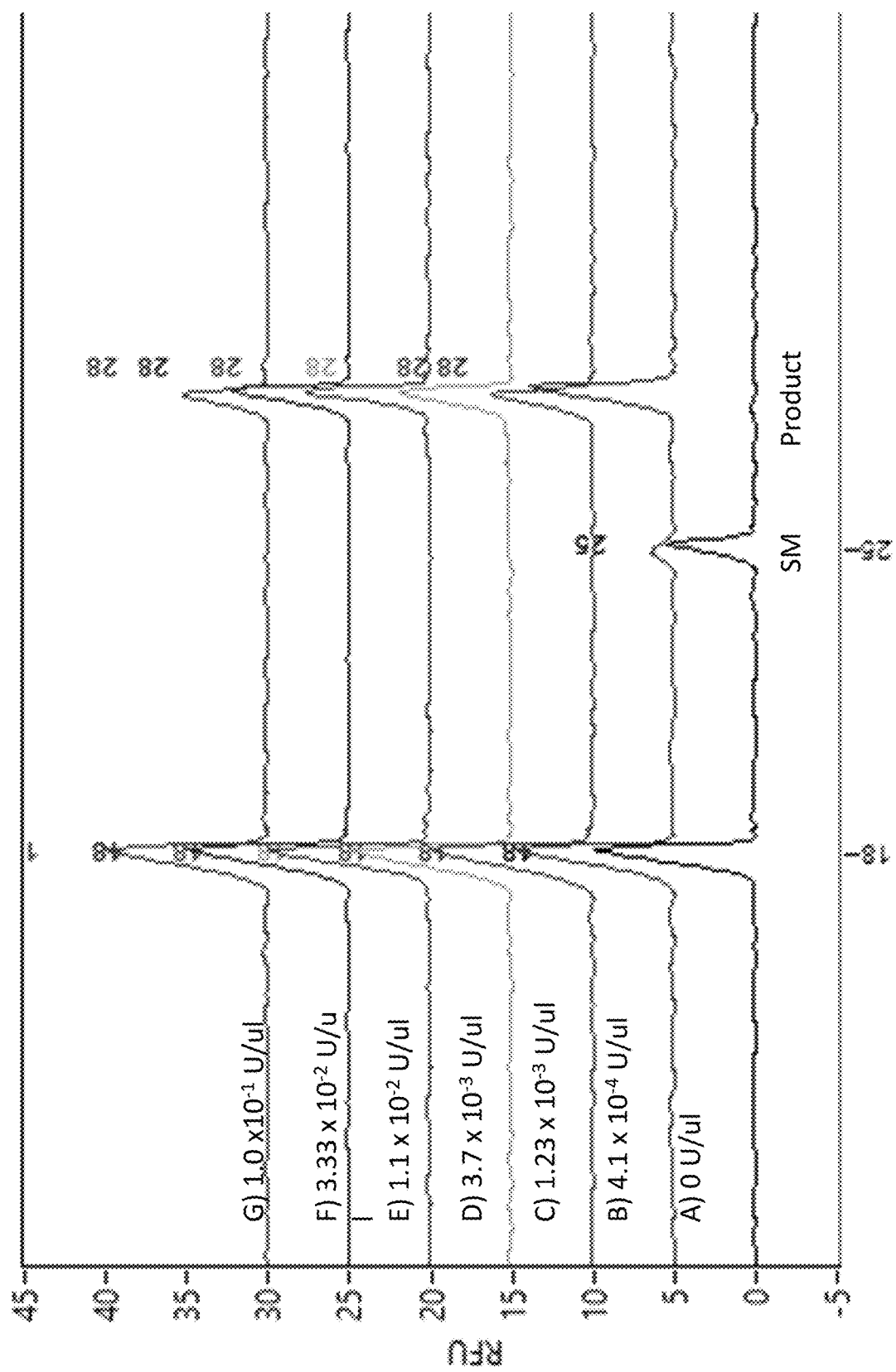

FIG. 14 shows CGE traces showing the removal of 3'-PO4 by treatment with Shrimp Alkaline Phosphatase. A) Chemically synthesized 5'-TAATAATAATAATAATTTTT-PO4-3' prior to treatment with Shrimp Alkaline Phosphatase and chemically synthesized 5'-TAATAATAATAATAATTTTT-PO4-3' after treatment with B) $4.1 \times 10^{-4}$ U/ul, C) $1.23 \times 10^{-3}$ U/ul, D) $3.7 \times 10^{-3}$ U/ul, E) $1.1 \times 10^{-2}$, F) $3.33 \times 10^{-2}$ U/ul, G) $1.0 \times 10^{-1}$ U/ul of Shrimp Alkaline Phosphatase for 1 minute at 37° C.

Figure 15:
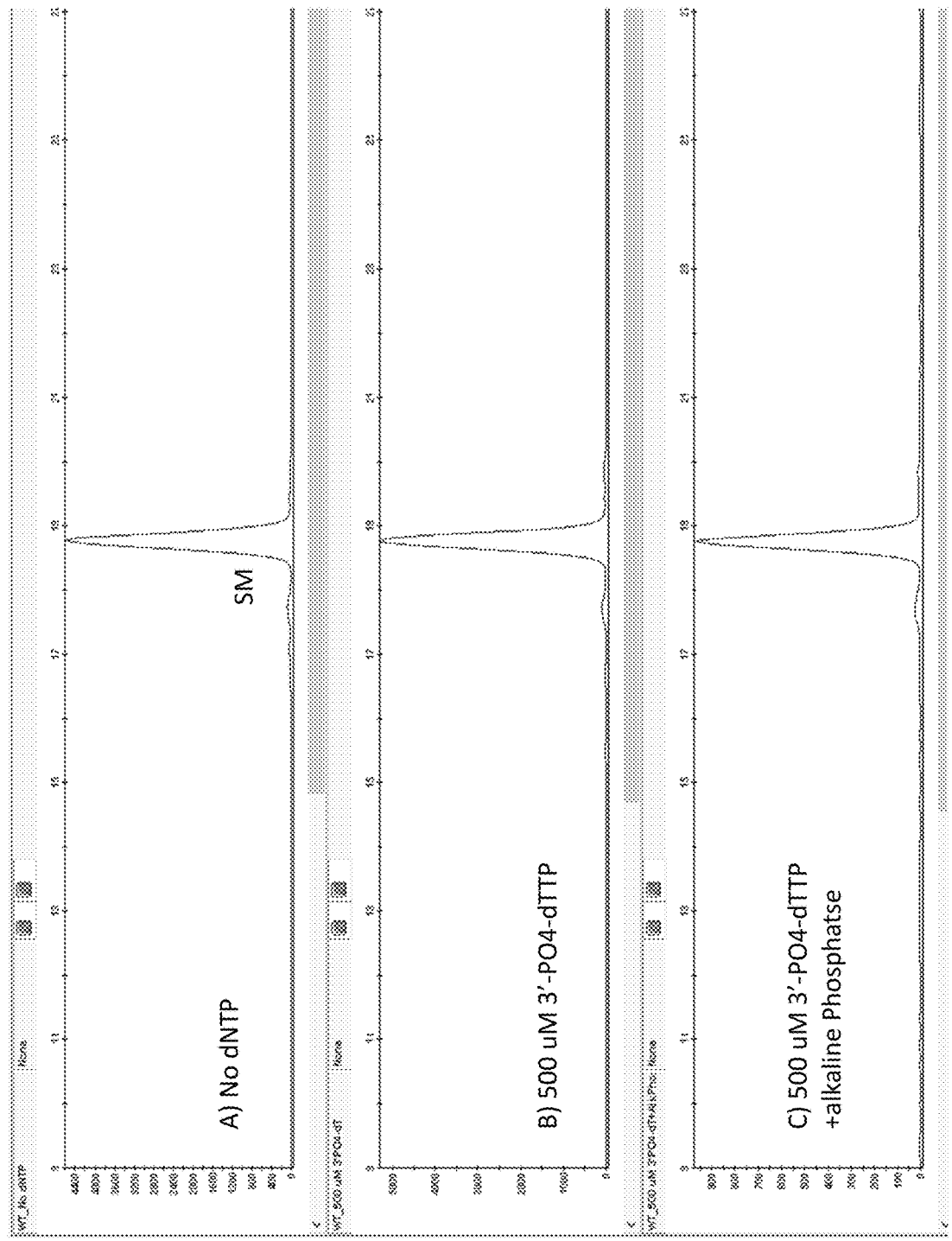

FIG. 15 shows CGE traces comparing: A) 5'-FAM-TAATAATAATAATAATTTTT after treatment with murine WT TdT and no dNTP; B) 5'-FAM-TAATAATAATAATAATTTTT after treatment with murine WT TdT and 500 uM 3'-PO4-dTTP for 60 minutes at 37° C.; C) 5'-FAM-TAATAATAATAATAATTTTT after treatment with murine WT TdT and 500 uM 3'-PO4-dTTP for 60 minutes at 37° C., followed by treatment with 0.2 units of Shrimp Alkaline Phosphatase for 15 minutes at 37° C.

Figure 16:
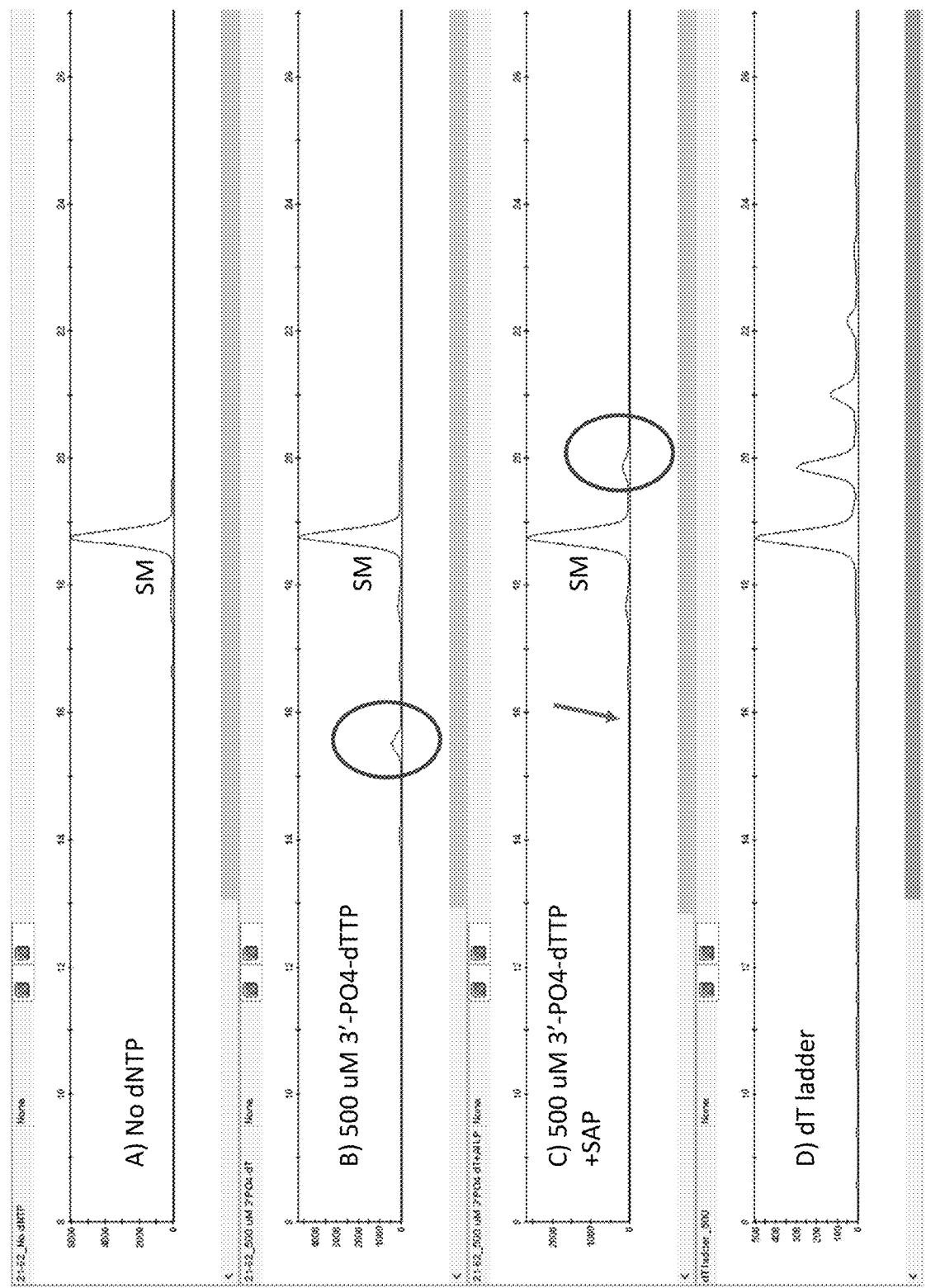

FIG. 16 shows CGE traces comparing A) 5'-FAM-TAATAATAATAATAATTTTT-3' after treatment with murine WT TdT and no dNTP for 60 minutes at 37° C.; B) 5'-FAM-TAATAATAATAATAATTTTT after treatment with murine TdT E180K+M192K+L381K+R454K+N474R and 500 uM 3'-PO4-dTTP for 60 minutes at 37° C.; C) 5'-FAM-TAATAATAATAATAATTTTT-3' after treatment with murine WT TdT and 500 uM 3'-PO4-dTTP for 60 minutes at 37° C., followed by treatment with 0.2 units of Shrimp Alkaline Phosphatase for 15 minutes at 37° C.; D) Homopolymer dT extension ladder created by treatment of 5'-FAM-TAATAATAATAATAATTTTT-3' with murine WT TdT and dTTP.

DESCRIPTION OF THE INVENTION

The invention facilitates the synthesis of polynucleotides, such as DNA, by providing modified enzymes that can be used with nucleic acid analogs. Using the disclosed methods, a modified template-independent terminal deoxynucleotidyl transferase (TdT) is obtained that allows the enzymatically mediated synthesis of de novo oligodeoxynucleotides, thereby enabling their use in routine assembly for gene synthesis. The enzymes of the invention lend themselves to aqueous-based, enzyme-mediated methods of synthesizing polynucleotides of a predetermined sequence on a solid support.

Figure 2:
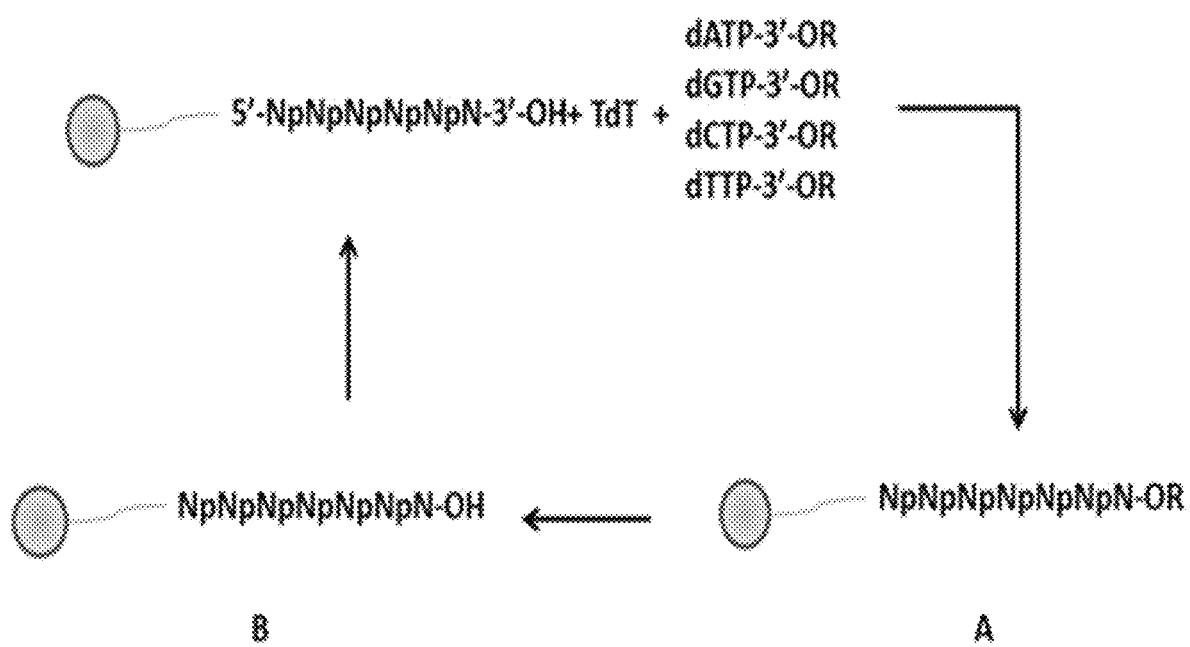
FIG. 2 illustrates an exemplary modified terminal deoxynucleotidyl transferase (TdT) mediated polynucleotide synthesis cycle using a support bound initiator and 3'-O-blocked nucleotide triphosphate including (A) incorporation of a nucleotide analog comprising a cleavable 3'-O-blocking group (indicated by R), and (B) removal of the 3'-O-blocking group thus enabling the next 3'-O-blocked nucleotide analog to be incorporated, wherein N=A, G, C, or T.

The modified enzymes of the invention will allow 3'-O-blocked dNTP analogs to be used in a step-by-step method to extend an initiating nucleic acid into a user defined sequence (see FIG. 2). Furthermore, after each nucleotide extension step, the reactants can be recovered and recycled from the solid support back to the original reagent reservoir. Once that step is complete, the 3'-O-blocking group will be removed, allowing the cycle to start anew. At the conclusion of n cycles of extension-recover-deblock-wash, the full length, single strand polydeoxynucleotide will be cleaved from the solid support and isolated for subsequent use. A variety of 3'-O-blocked deoxynucleotides, may be used, but the choice of specific 3'-O-blocking groups is dictated by: 1) the smallest possible bulk to maximize substrate utilization by TdT and 2) removal of the blocking group with the mildest and preferably aqueous conditions in the shortest period of time.

Cost savings by this approach will be achieved by exploiting the higher yield of final oligonucleotide product at a lower starting scale than currently being used as the existing industry standard (i.e., less than 1 nanomole). Future adaptation of this enzymatic approach to array based formats will allow even further and more dramatic reductions in the cost of synthesis of long oligonucleotides achievable by highly parallel synthesis. Furthermore, the enzymatic synthesis process that we propose uses only aqueous based chemistries like buffers and salts, thus greatly reducing the environmental burden of the organic waste generated by the existing phosphoramidite method.

Figure 1:
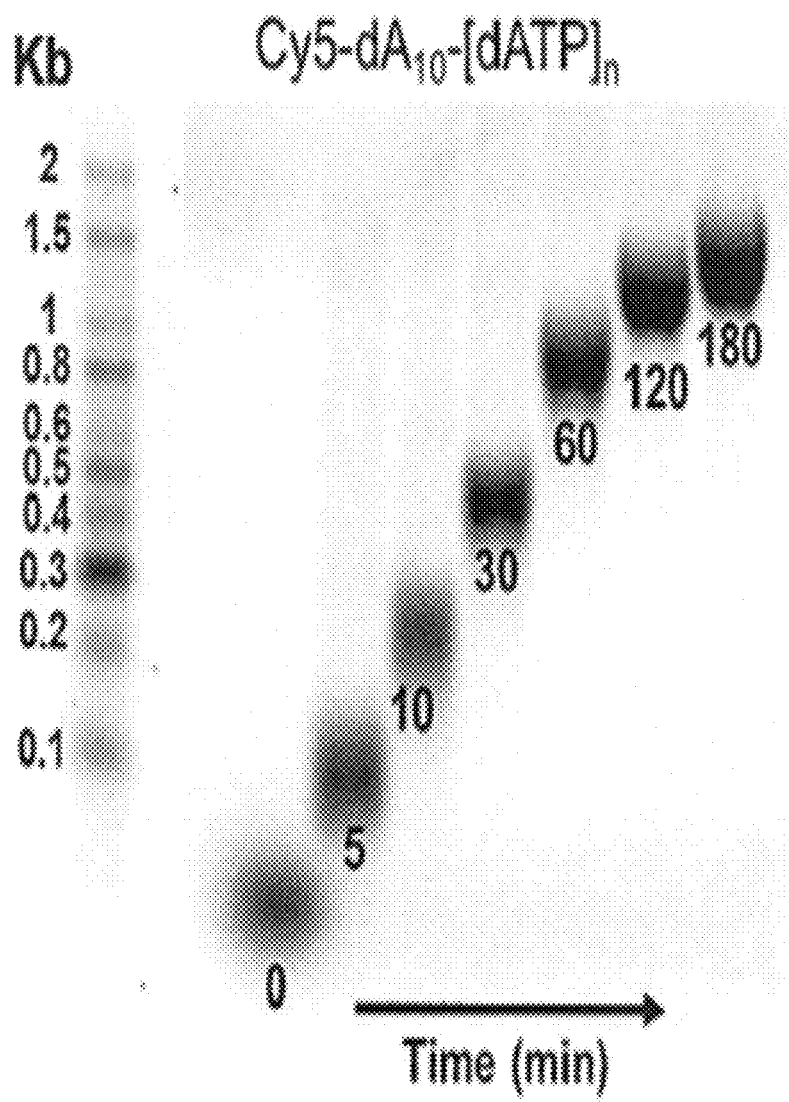
FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points from Tjong et al. "Amplified on-chip fluorescence detection of DNA hybridization by surface-initiated enzymatic polymerization," *Anal. Chem.*, 2011; 83:5153-5159 (2011).

The methods of the invention may be used to modify terminal deoxynucleotidyl transferases (TdT), however other enzymes could be modified with similar methods. TdT is likely to be a successful starting enzyme because it is capable of 3'-extension activity using single strand initiating primers in a template-independent polymerization. However, prior to the invention described herein, there have been no reports of 3'-O-blocked nucleotides being incorporated into single-stranded oligonucleotide by an enzyme in the absence of a template. In fact, as Chang and Bollum reported, substitution of the 3'-hydroxyl group results in complete inactivity of available transferase enzymes. See Chang and Bollum, "Molecular Biology of Terminal Transferase, *CRC Critical Reviews in Biochemistry*, vol. 21 (1), p. 27-52 (1986), incorporated herein by reference in its entirety. Nonetheless, when TdT is used with natural dNTPs (i.e., not 3'-O-blocked), and without a template, oligonucleotide extension continues without stopping. Such uncontrolled incorporation is evidenced by the time-dependent gel electrophoresis images shown in FIG. 1. FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points. (Adapted with permission from Tjong et al. "Amplified on-chip fluorescence detection of DNA hybridization by surface-initiated enzymatic polymerization," *Anal. Chem.*, 2011; 83:5153-5159 (2011), incorporated by reference herein in its entirety.) Additionally, TdT can extend primers in a near quantitative manner resulting in the addition of thousands of nucleotides, while TdT is likely to accept a wide variety of modified and substituted dNTPs as efficient substrates. Furthermore, a substantial library of mechanistic and structural information regarding TdT already exists. See Delarue et al., *EMBO J.* 2002; 21(3):427-39; Gouge et al., *J Mol Biol.* 2013 Nov. 15; 425(22):4334-52 and Romain et al., *Nucleic Acids Res.* 2009; 37(14):4642-56, both of which are incorporated by reference in their entireties.

It is known that TdT can use substrates having modifications and/or substitutions at the deoxyribose sugar ring as well as the purine/pyrimidine nucleobases. For example, TdT accepts bulky modifications at the C5 of pyrimidines and the C7 of purines. See Sorensen et al., "Enzymatic Ligation of Large Biomolecules to DNA," *ACS Nano* 2013, 7(9):8098-104; Figeys et al., *Anal. Chem.* 1994, 66(23): 4382-3; Li et al., *Cytometry,* 1995, 20(2):172-80, all of which are incorporated by reference in their entireties. In some instances, TdT can even accept non-nucleotide triphosphates. See Barone et al., *Nucleotides and Nucleic Acids* 2001, 20(4-7):1141-5, and Alexandrova et al., *Bioconjug Chem.,* 2007, 18(3):886-93, both of which are incorporated by reference in their entireties. However, there is little evidence in the prior art that TdT can accept 3'-O-blocked nucleotides. See, for example, Knapp et al., *Chem. Eur. J.,* 2011, 17:2903, incorporated herein by reference in its entirety. While the lack of activity of TdT was not a focus of Knapp et al., the authors reported that they tested their 3'-OH modified analog with TdT, and saw no incorporation of this relatively small 3'-OH modification into an oligonucleotide.

Native TdT is a very efficient enzyme. It has been demonstrated that TdT can polymerize extremely long homopolydeoxynucleotides of 1000 to 10,000 nucleotides in length (see Hoard et al., *J of Biol Chem,* 1969 244(19):5363-73; Bollum, *The Enzymes,* Volume 10, New York: Academic Press; 1974. p. 141-71; Tjong et al., *Anal Chem,* 2011, 83:5153-59, all of which are incorporated by reference in their entireties). Random sequence oligomers consisting of all four nucleotides have also been polymerized by TdT, however there are no reports of ordered polynucleotides being synthesized in the absence of a template. See Damiani, et al., *Nucleic Acids Res,* 1982, 10(20):6401-10, incorporated by reference herein in its entirety. Support-bound synthesis of polynucleotides by TdT is additionally supported by reports of homopolymer synthesis of 150 bps initiators covalently attached to self-assembled monolayers on gold surfaces. See Chow et al., *J Am Chem Soc* 2005; 127:14122-3, and Chow and Chilikoti, *Langmuir* 2007, 23:11712-7, both of which are incorporated by reference in their entireties. These authors also observed preference by TdT of dATP>dTTP>>dGTP≈dCTP for incorporation of homopolymers. In a more recent report, Tjong et al. demonstrated the TdT mediated synthesis of long (>1 Kb) homopolymer ssDNA from initiator primers immobilized on glass surfaces.

Figure 3:
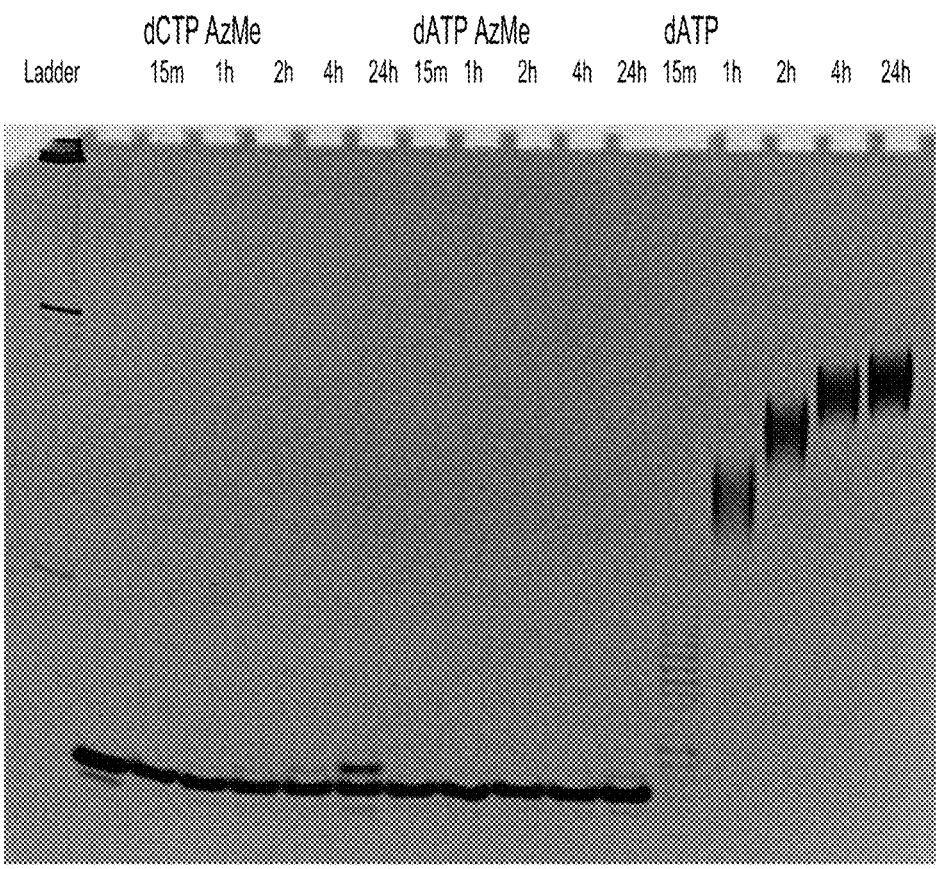
FIG. 3 shows the polyacrylamide gel analysis of a solution phase reaction time course of commercially-available TDT and a nucleic acid initiator with 3'-O-azidomethyl-dCTP or 3'-O-azidomethyl-dATP. Lane 1—100 bp ladder size standard, Lane 2—oligonucleotide standard, Lane 3—3'-O-azidomethyl-dCTP+TdT 15' reaction time, Lane 4—1 hour, Lane 5—2 hours, Lane 6—4 hours, Lane 7—24 hours, Lane 8—3'-O-azidomethyl-dATP+TdT 15' reaction time, Lane 9—1 hour, Lane 10—2 hours, Lane 10—4 hours, Lane 11—24 hours, Lane 12—dATP+TdT 15' reaction time, Lane 13—1 hour, Lane 14—4 hours, Lane 15—24 hours.

The distributive behavior of TdT is reinforced by FIG. 3, which shows a time course of a solution phase synthesis of 1-1.5 kb homopolymers. After each addition of an unmodified (natural) dNTP, the enzyme dissociates, thus allowing the random extension of any strand in the population. The distribution of product lengths in such a system should follow a Poisson distribution, as reported by Bollum and co-workers in 1974. If TdT were used with a terminating nucleotide species, i.e., one with the 3'-O-position blocked, the reaction should proceed to completion, resulting not in a distribution of product lengths, but essentially a pure product of a single nucleotide addition.

Nonetheless, as described above, nucleotide synthesis with 3'-O-blocked dNTPs does not proceed with commercially-available TdT proteins. This fact is reinforced by FIG. 3, which shows a gel shift assay used to monitor the solution phase incorporation kinetics of 3'-O-azidomethyl dATP and 3'-O-azidomethyl dCTP using a commercially-available, recombinant TdT. The data in FIG. 3 clearly show that neither 3'-O-modified dNTP analog is a substrate for TdT, i.e., there is no polynucleotide extension when compared to reactions containing dATP as a positive control (lanes 12 thru 15). FIG. 3, thus, adds further evidence that commercially-available TdTs are not able to synthesize oligomers by incorporating dNTPs with modified 3'-OHs.

With suitable modifications, a variety of different 3'-O-blocked dNTP analogs will be suitable for the controlled addition of nucleotides by TdT. Modified 3'-O-blocked dNTP analogs include, but are not limited to, the 3'-O-allyl, 3'-O-azidomethyl, 3'-O—$NH_2$, 3'-O—$CH_2N_3$, 3'-O—ONHC(O)H, 3'-O—$CH_2SSCH_3$, and 3'-O—$CH_2CN$ blocking groups. Overall, the choice of the 3'-O-blocking group will be dictated by: 1) the smallest possible bulk to maximize substrate utilization by TdT, which is likely to affect kinetic uptake, and 2) the blocking group with the mildest removal conditions, preferably aqueous, and in the shortest period of time. 3'-O-blocking groups that are the suitable for use with this invention are described in WO 2003/048387; WO 2004/018497; WO 1996/023807; WO 2008/037568; Hutter D, et al. *Nucleosides Nucleotides Nucleic Acids,* 2010, 29(11): 879-95; and Knapp et al., *Chem. Eur. J.,* 2011, 17:2903, all of which are incorporated by reference in their entireties.

Figure 4:
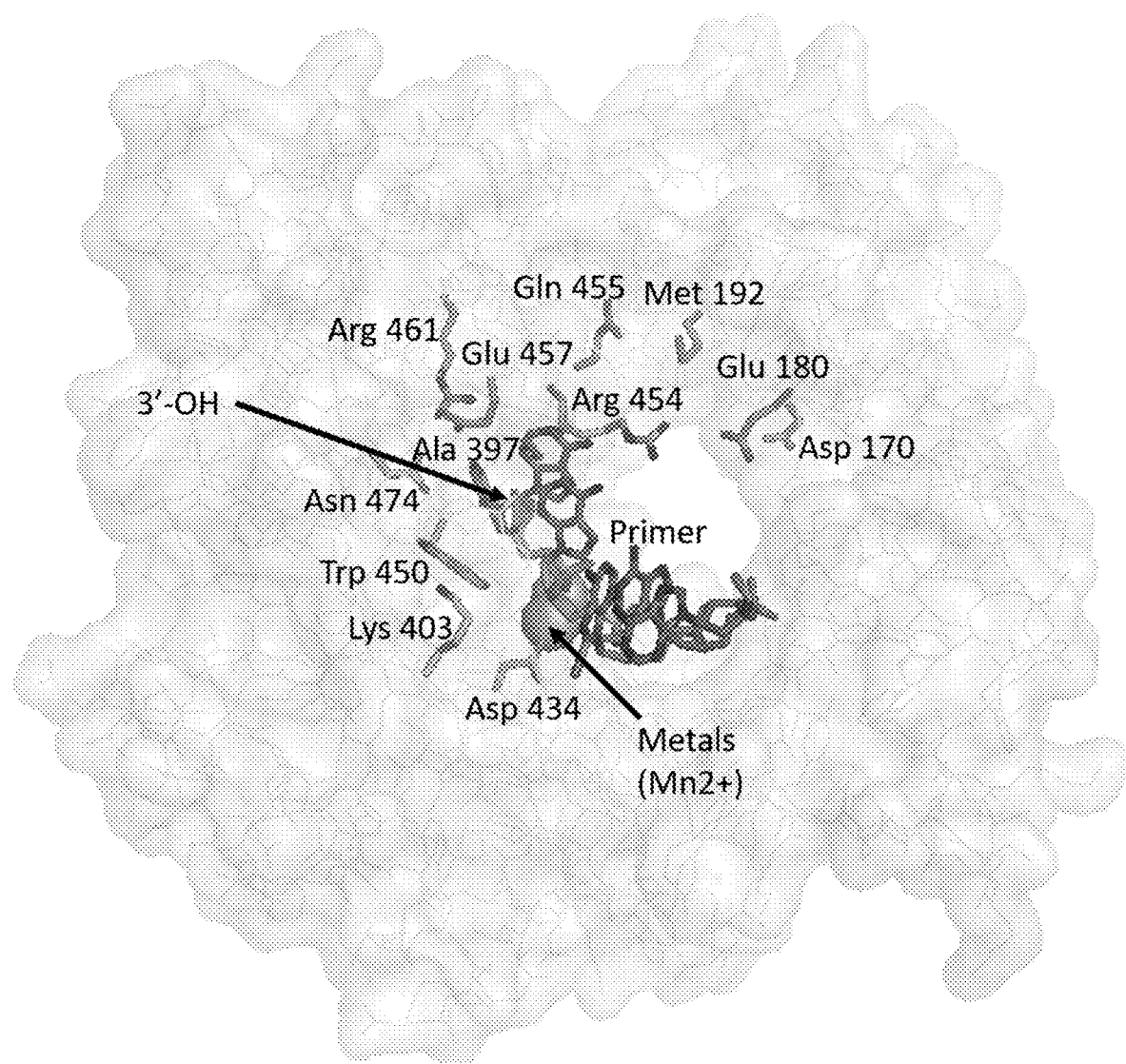
FIG. 4 shows a computer-generated image of the active site of TdT using the PDB crystal structure 4I29, showing the computationally docked catalytically productive position a 3'-O-dATP analog (blue, red, orange frame), each complexed to the two active-site metal ions (large greenspheres).

A computational model of the active site of murine TdT was created to understand the structural basis for the lack of utilization of 3'-O-blocked dNTPs by TdT. Additionally, the computer model made it possible to "fit" various modified dNTPs into the active site. FIG. 4 shows the docking of a -dATP (shown in blue, red, magenta, orange) with murine TdT (see SEQ ID NO. 9, below) using the PDB crystal structure 4I29 and AutoDock 4.2 (Molecular Graphics Laboratory, Scripps Research Institute, La Jolla, Calif.).

The phosphate portions of the dATPs (orange) are in complex with the catalytic metal ions (green) while the alpha phosphate is positioned to be attacked by the 3'-OH of the bound oligonucleotide. The model shown in FIG. 4 indicates the choice of amino acid residues likely to interfere with the formation of a catalytically productive complex when a 3'-O-blocked dNTP is present. Other residues that may interact with the closest residues, like Glu 180 or Met 192, are also targets of modification. Amino acid numbering and positions are provided with reference to the murine TdT of SEQ ID NO. 9 but the referenced amino acid modifications are applicable to any TdT having similar sequence including the GGFRR or TGSR motifs.

AutoDock's predicted binding mode suggests that modification to the 3'-OH will change the electrostatic interactions between two residues, Arg336 and Arg454. Although Arg336 is near the reaction center in the active site, Arg 336 is highly conserved, and early studies found that replacement of Arg336 with Gly or Ala reduced dNTP activity by 10-fold (Yang B et al. J. Mol. Biol. 1994; 269(16):11859-68). Accordingly, one motif for modification is the GGFRR motif including Arg 336 in the above structural model.

Additionally, it is thought that Gly452 and Ser453 exist in a cis-peptide bond conformation (see Delarue et al., *EMBO J.,* 2002; 21(3):427-39, incorporated herein by reference in its entirety) and that the guanidinium group of Arg336 assists in the stabilization of this conformation. The stability provided by Arg336 may help explain why substitutions at this position have a negative impact on the reactivity of modified TdT proteins. In some instances, the instability created by modifying position 336 may be overcome by using proline residues to stabilize cis-peptide bond conformation. However, if Arg336 is substituted, e.g., with alanine or glycine, the entire TGSR motif (positions 451, 452, 435, 454) may also have to be modified to compensate for this change. For example, the TGSR motif may be modified to TPSR or TGPR. Accordingly, the TGSR motif, including Gly452 in the above structural model was targeted for modification.

On the other hand, sequence analysis of the TdT family demonstrates a wide range of amino acids that can be accommodated at position 454. This analysis suggests structural flexibility at position 454, and surrounding residues. In another embodiment, substitutions at Arg454 to accommodate the steric bulk of a 3'-0-blocking group may require additional modifications to the α14 region to compensate for substitutions of glycine or alanine at Arg454. In other embodiments, substitutions to other residues in the all region may be required to compensate for substitution to Arg336 either instead of, or in addition to, modification of the TGSR motif.

While modification to Arg336 and Arg454 may change the binding interactions of 3'-O-modified dNTPs, it may also be necessary to explore substitutions that would result in improved steric interactions of 3'-O-modified dNTPs with TdT. In order to test computationally predicted enzyme variants that show increased substrate utilization of 3'-O-blocked dNTPs, synthetic genes specifying specific amino acid substitutions were generated in appropriate plasmid vectors and introduced into cells. After expression and isolation, protein variants were screened for activity by a polymerase incorporation assay with selected 3'-O-blocked dNTP analogs. FIG. 5 shows the results of the screening of various synthetically generated murine TdT variants. In some embodiments, single amino acid changes are important while in other, combinations of one & two amino acids also produce increased incorporation of 3'-O-blocked dNTPs. Interactions with residues such as Gly332, Gly333, Gly452, Thr451, Trp450, Ser453, and Q455 of murine TdT are important. Each of these residues is within 0.6 nm of the 3'-OH of a typical dNTP. These residues are also potential targets for substitution to allow the extra steric bulk of a 3'-blocking group like 3'-O-azidomethyl or 3'-O-aminoxy. Residues that are within 1.2 nm of the 3'-OH such as Glu457, Ala510, Asp509, Arg508, Lys199, Ser196, Met192, Glu180 or Leu161 may also potentially interfere with the substrate utilization of a 3'-O-blocked dNTP and are thus targets for substitution in addition to or in combination with Arg336 and Arg454. Additional residues of interest include Arg461 and Asn474.

While the TGSR and GGFRR motifs are highlighted here, modifications to the flanking amino acids such as Thr331, Gly337, Lys338, Gly341, or His342 are also contemplated for providing (alone or in combination) increased incorporation of 3'-O-blocked dNTPs as discussed herein. Various in silico modeled TdT modifications capable of increased incorporation are discussed in Example 2 below.

In addition to amino acid substitutions at positions 500-510 it may be necessary to delete residues to remove interference with a 3'-O-blocking group. Since these amino acids are located near the C-terminus of the protein, and exist in a relatively unstructured region, they may be deleted singly or altogether, either instead of or in combination with the modifications described above. In certain embodiments, insertion of residues into the modified TdT. For example, insertions of residues in the GGFRR or TGSR motifs or flanking regions can allow an increased rate of incorporation of 3'-O-blocked dNTP by the modified TdT. TdT modifications can include insertion of a Tyrosine residue between the Phe334 and Arg335 residues (or substitutions thereof) of the GGFRR motif.

Modified TdT's of the invention include those described in FIG. 5. Modified TdT's may include one or more of a modification to Glu180 including E180L, E180R, E180D, or E180K. Contemplated modifications to Met192 include, for example, M192E, M192W, M192K, or M192R. Contemplated modifications to Gln455 include, for example, Q455I. Contemplated modifications to Trp450 include, for example, W450H. Contemplated modifications to ARG454 include, for example, R454I, R454K, R454A, or R454T. Contemplated modifications to Arg461 include, for example, R461V and modifications to Asn474 may include N474R. In various embodiments combinations of two or more modified residues may be used such as, for example, E180D+W450H, E180K+R454A, M192K+E180K, E180K+R454I, E180D+M192E, E180D+M192E+R454T, or E180K+W450H.

As shown below, most TdTs include the GGFRR and TGSR motifs. In the following sequences, the GGFRR and TGSR motifs have been bolded and underlined for easy reference. Native calf thymus TdT is a candidate for alteration of the primary structure to achieve a suitable template-independent polymerase. However, a variety of other proteins may be explored to identify a candidate suitable for the use with 3'-O-blocked dNTP analogs, including human and murine TdT. The amino acid sequence corresponding to native calf TdT is listed in Table 1 as SEQ ID NO. 1, while the nucleic acid sequence is listed in Table 2 as SEQ ID NO. 2. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NO. 1. Furthermore, it may be possible to truncate portions of the amino acid sequence of bovine TdT and still maintain catalytic activity.

TABLE 1

Amino Acid Sequence of Bovine TdT

SEQ ID NO. 1: (520 aa)

| | | | |
|---|---|---|---|
| MAQQRQHQRL | PMDPLCTASS | GPRKKRPRQV | GASMASPPHD |
| IKFQNLVLFI | LEKKMGTTRR | NFLMELARRK | GFRVENELSD |
| SVTHIVAENN | SGSEVLEWLQ | VQNIRASSQL | ELLDVSWLIE |
| SMGAGKPVEI | TGKHQLVVRT | DYSATPNPGF | QKTPPLAVKK |
| ISQYACQRKT | TLNNYNHIFT | DAFEILAENS | EFKENEVSYV |
| TFMRAASVLK | SLPFTIISMK | DTEGIPCLGD | KVKCIIEEII |
| EDGESSEVKA | VLNDERYQSF | KLFTSVFGVG | LKTSEKWFRM |
| GFRSLSKIMS | DKTLKFTKMQ | KAGFLYYEDL | VSCVTRAEAE |
| AVGVLVKEAV | WAFLPDAFVT | MTGGFRRGKK | IGHDVDFLIT |
| SPGSAEDEEQ | LLPKVINLWE | KKGLLLYYDL | VESTFEKFKL |
| PSRQVDTLDH | FQKCFLILKL | HHQRVDSSKS | NQQEGKTWKA |
| IRVDLVMCPY | ENRAFALLGW | TGSRQFERDI | RRYATHERKM |
| MLDNHALYDK | TKRVFLKAES | EEEIFAHLGL | DYIEPWERNA |

TABLE 2

Nucleic Acid Sequence of Bovine TdT

SEQ ID NO. 2: (1923 nt)

```
ctcttctgga gataccactt gatggcacag cagaggcagc
atcagcgtct tcccatggat ccgctgtgca cagcctcctc
aggccctcgg aagaagagac ccaggcaggt gggtgcctca
atggcctccc ctcctcatga catcaagttt caaaatttgg
tcctcttcat tttggagaag aaaatgggaa ccacccgcag
aaacttcctc atggagctgg ctcgaaggaa aggtttcagg
gttgaaaatg agctcagtga ttctgtcacc cacattgtag
cagaaaacaa ctctggttca gaggttctcg agtggcttca
ggtacagaac ataagagcca gctcgcagct agaactcctt
gatgtctcct ggctgatcga aagtatggga gcaggaaaac
cagtggagat tacaggaaaa caccagcttg ttgtgagaac
agactattca gctacccccaa acccaggctt ccagaagact
ccaccacttg ctgtaaaaaa gatctcccag tacgcgtgtc
aaagaaaaac cactttgaac aactataacc acatattcac
ggatgccttt gagatactgg ctgaaaattc tgagtttaaa
gaaaatgaag tctcttatgt gacatttatg agagcagctt
ctgtacttaa atctctgcca ttcacaatca tcagtatgaa
ggatacagaa ggaattcccc gcctggggga caaggtgaag
tgtatcatag aggaaattat tgaagatgga gaaagttctg
aagttaaagc tgtgttaaat gatgaacgat atcagtcctt
caaactcttt acttcgtgtt ttgggagtgg actgaagaca
tctgagaaat ggttcaggat ggggttcaga tctctgagta
aaataatgtc agacaaaacc ctgaaattca caaaaatgca
gaaagcagga tttctctatt atgaagacct tgtcagctgc
gtgaccaggg ccgaagcaga ggcggttggc gtgctggtta
aagaggctgt gtgggcattt ctgccggatg cctttgtcac
catgacagga ggattccgca ggggtaagaa gattgggcat
gatgtagatt ttttaattac cagcccagga tcagcagagg
atgaagagca acttttgcct aaagtgataa acttatggga
aaaaaaggga ttacttttat attatgacct tgtgagtca
acatttgaaa agttcaagtt gccaagcagg caggtggata
ctttagatca ttttcaaaaa tgctttctga ttttaaaatt
gcaccatcag agagtagaca gtagcaagtc caaccagcag
gaaggaaaga cctggaaggc catccgtgtg gacctggtta
tgtgcccta cgagaaccgt gcctttgccc tgcctaggctg
gactggctcc cggcagtttg agagagacat ccggcgctat
gccacacacg agcggaagat gatgctggat aaccacgctt
tatatgacaa gaccaagagg gtatttctca aagcggaaag
tgaagaagaa atctttgcac atctgggatt ggactacatt
gaaccatggg aaagaaatgc ttaggagaaa gctgtcaact
ttttctttt ctgttctttt tttcaggtta gacaaattat
gcttcatatt ataatgaaag atgccttagt caagtttggg
attctttaca ttttaccaag atgtagattg cttctagaaa
taagtagttt tggaaacgtg atcaggcacc ccctgggtta
tgctctggca agccatttgc aggactgatg tgtagaactc
gcaatgcatt ttccataggaa acagtgttgg aattggtggc
tcatttccag ggaagttcat caaagcccac tttgcccaca
gtgtagctga aatactgtat acttgccaat aaaaatagga
aac
```

Additionally, to make isolation of recombinant proteins easier, it is common to append an N-terminal His tag sequence to the recombinant protein (see Boule J-B et al., *Molecular Biotechnology*, 1998; 10:199-208, incorporated by reference herein in its entirety), which is used in combination with an affinity column (Hitrap, Amersham Pharmacia Biotech, Uppsala, Sweden). Alternatively, N-terminal truncated forms of the enzyme with appended His-tag sequence will work with the current invention (see, e.g., U.S. Pat. No. 7,494,797, incorporated by reference herein in its entirety). His-tagged Bovine TdT amino acid sequences are shown below in Tables 3, 5, and 7, while His-tagged Bovine TdT nucleic acid sequences are shown below in Tables 4, 6, and 8. His tags may be engineered at other positions as required. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NOS. 3, 5, or 7.

TABLE 3

Amino Acid Sequence of a 4138 and His-tagged Bovine TdT.

SEQ ID No. 3: (392 aa)

```
Met Arg Gly Ser His His His His His His Arg Thr
Asp Tyr Ser Ala Thr Pro Asn Pro Gly Phe Gln Lys
Thr Pro Pro Leu Ala Val Lys Lys Ile Ser Gln Tyr
Ala Cys Gln Arg Lys Thr Thr Leu Asn Asn Tyr Asn
His Ile Asp Ala Phe Glu Ile Leu Ala Glu Asn Ser
Glu Phe Lys Glu Asn Glu Val Ser Tyr Val Thr Phe
Met Arg Ala Ala Ser Val Leu Lys Ser Leu Pro Phe
Thr Ile Ile Ser Met Lys Asp Thr Phe Thr Glu Gly
Ile Pro Cys Leu Gly Asp Lys Val Lys Cys Ile Ile
Glu Glu Ile Ile Glu Asp Gly Glu Ser Ser Glu Val
Lys Ala Val Leu Asn Asp Glu Arg Tyr Gln Ser Phe
Lys Leu Ser Val Phe Gly Val Gly Leu Lys Thr Ser
Glu Lys Trp Phe Arg Met Gly Phe Thr Phe Arg Ser
Leu Ser Lys Ile Met Ser Asp Lys Thr Leu Lys Lys
Met Gln Lys Ala Gly Phe Leu Tyr Tyr Glu Asp Leu
Val Ser Cys Val Thr Arg Ala Glu Ala Glu Ala Val
Gly Val Leu Val Lys Glu Ala Val Trp Ala Phe Leu
Pro Asp Ala Phe Val Thr Met Thr **Gly Gly Phe Arg
Arg** Gly Lys Lys Ile Gly His Asp Val Asp Phe Leu
Ile Thr Ser Pro Gly Ser Ala Glu Asp Glu Glu Gln
Leu Leu Pro Lys Val Ile Asn Leu Trp Glu Lys Lys
Gly Leu Leu Leu Tyr Tyr Asp Leu Val Glu Ser Thr
Phe Glu Lys Phe Lys Phe Thr Leu Pro Ser Arg Gln
Val Asp Thr Leu Asp His Phe Gln Lys Cys Phe Leu
Ile Leu Lys Leu His His Gln Arg Val Asp Ser Ser
Lys Ser Asn Gln Gln Glu Gly Lys Thr Trp Lys Ala
Ile Arg Val Asp Leu Val Met Cys Pro Tyr Glu Asn
Arg Ala Phe Ala Leu Leu Gly Trp Thr Gly Ser Arg
Gln Phe Glu Arg Asp Ile Arg Arg Tyr Ala Thr His
Glu Arg Lys Met Met Leu Asp Asn His Ala Leu Tyr
Asp Lys Thr Lys Arg Val Phe Leu Lys Ala Glu Ser
Glu Glu Glu Ile Phe Ala His Leu Gly Leu Asp Tyr
Ile Glu Pro Trp Glu Arg Asn Ala
```

TABLE 4

Nucleotide Sequence of a 4138 and His-tagged Bovine TdT.

SEQ ID No. 4: (1187 nt)

```
atgagaggat cgcatcacca tcaccatcac agaacagact
attcagctac cccaaaccca ggcttccaga agactccacc
acttgctgta aaaaagatct cccagtacgc gtgtcaaaga
aaaaccactt tgaacaacta taaccacata ttcacggatg
cctttgagat actggctgaa aattctgagt ttaaagaaaa
tgaagtctct tatgtgacat ttatgagagc agcttctgta
cttaaatctc tgccattcac aatcatcagt atgaaggata
cagaaggaat tcctgcctg ggggacaagg tgaagtgtat
catagaggaa attattgaag atggagaaag ttctgaagtt
aaagctgtgt taaatgatga acgatatcag tccttcaaac
tctttacttc tgtttttgga gtgggactga agacatctga
gaaatggttc aggatggggt tcagatctct gagtaaaata
atgtcagaca aaaccctgaa attcacaaaa atgcagaaag
caggatttct ctattatgaa gaccttgtca gctgcgtgac
cagggccgaa gcagaggcgg ttggcgtgct ggttaaagag
gctgtgtggg catttctgcc ggatgccttt gtcaccatga
caggaggatt ccgcaggggt aagaagattg ggcatgatgt
agatttttta attaccagcc caggatcagc agaggatgaa
gagcaacttt tgcctaaagt gataacttta tgggaaaaaa
agggattact tttatattat gaccttgtgg agtcaacatt
tgaaaagttc aagttgccaa gcaggcaggt ggatacttta
gatcatttc aaaaatgctt tctgatttta aaattgcacc
atcagagagt agacagtagc aagtccaacc agcaggaaga
aaagacctgg aaggccatcc gtgtggacct ggttatgtgc
ccctacgaga accgtgcctt tgccctgcta ggctggactg
gctcccggca gtttgagaga gacatccggc gctatgccac
acacgagcgg aagatgatgc tggataacca cgctttatat
gacaagacca agagggtatt tctcaaagcg gaaagtgaag
aagaaatctt tgcacatctg ggattggact acattgaacc
atgggaaaga aatgcttaag cttgcgc
```

TABLE 5

Amino Acid Sequence of a 4151 and His-tagged Bovine TdT.

SEQ ID No. 5: (379 aa)

Met Arg Gly Ser His His His His His His Lys Thr
Pro Pro Leu Ala Val Lys Lys Ile Ser Gln Tyr Ala
Cys Gln Arg Lys Thr Thr Leu Asn Asn Tyr Asn His
Ile Asp Ala Phe Glu Ile Leu Ala Glu Asn Ser Glu
Phe Lys Glu Asn Glu Val Ser Tyr Val Thr Phe Met
Arg Ala Ala Ser Val Leu Lys Ser Leu Pro Phe Thr
Ile Ile Ser Met Lys Asp Thr Phe Thr Glu Gly Ile
Pro Cys Leu Gly Asp Lys Val Lys Cys Ile Ile Glu
Glu Ile Ile Glu Asp Gly Glu Ser Ser Glu Val Lys
Ala Val Leu Asn Asp Glu Arg Tyr Gln Ser Phe Lys
Leu Ser Phe Gly Val Gly Leu Lys Thr Ser Glu Lys
Lys Trp Phe Arg Met Gly Phe Thr Phe Arg Ser Leu
Ser Lys Ile Met Ser Asp Lys Thr Leu Lys Lys Met
Gln Lys Ala Gly Phe Leu Tyr Tyr Glu Asp Leu Val
Ser Cys Val Thr Arg Ala Glu Ala Glu Ala Val Gly
Val Leu Val Lys Glu Ala Val Trp Ala Phe Leu Pro
Asp Ala Phe Val Thr Met Thr Gly Gly Phe Arg Arg
Gly Lys Lys Ile Gly His Asp Val Asp Phe Leu Ile
Thr Ser Pro Gly Ser Ala Glu Asp Glu Glu Gln Leu
Leu Pro Lys Val Ile Asn Leu Trp Glu Lys Lys Gly
Leu Leu Leu Tyr Tyr Asp Leu Val Glu Ser Thr Phe
Glu Lys Phe Lys Phe Pro Ser Arg Gln Val
Asp Thr Leu Asp His Phe Gln Lys Cys Phe Leu Ile
Leu Lys Leu His His Gln Arg Val Asp Ser Ser Lys
Ser Asn Gln Gln Glu Gly Lys Thr Trp Lys Ala Ile
Arg Val Asp Leu Val Met Cys Pro Tyr Glu Asn Arg
Ala Phe Ala Leu Leu Gly Trp Thr Gly Ser Arg Gln
Phe Glu Arg Asp Ile Arg Arg Tyr Ala Thr His Glu
Arg Lys Met Met Leu Asp Asn His Ala Leu Tyr Asp
Lys Thr Lys Arg Val Phe Leu Lys Ala Glu Ser Glu
Glu Glu Ile Phe Ala His Leu Gly Leu Asp Tyr Ile
Glu Pro Trp Glu Arg Asn Ala

TABLE 7

Amino Acid Sequence of a 4160 and His-tagged Bovine TdT.

SEQ ID No. 7: (370 aa)

Met Arg Gly Ser His His His His His His Ile Ser
Gln Tyr Ala Cys Gln Arg Lys Thr Thr Leu Asn Asn
Tyr Asn His Ile Asp Ala Phe Glu Ile Leu Ala Glu
Asn Ser Glu Phe Lys Glu Asn Glu Val Ser Tyr Val
Thr Phe Met Arg Ala Ala Ser Val Leu Lys Ser Leu
Pro Phe Thr Ile Ile Ser Met Lys Asp Thr Phe Thr
Glu Gly Ile Pro Cys Leu Gly Asp Lys Val Lys Cys
Ile Ile Glu Glu Ile Ile Glu Asp Gly Glu Ser Ser
Glu Val Lys Ala Val Leu Asn Asp Glu Arg Tyr Gln
Ser Phe Lys Leu Ser Phe Gly Val Gly Leu Lys Lys
Thr Ser Glu Lys Trp Phe Arg Met Gly Phe Thr Phe
Arg Ser Leu Ser Lys Ile Met Ser Asp Lys Thr Leu
Lys Lys Met Gln Lys Ala Gly Phe Leu Tyr Tyr Glu
Asp Leu Val Ser Cys Val Thr Arg Ala Glu Ala Glu
Ala Val Gly Val Leu Val Lys Glu Ala Val Trp Ala
Phe Leu Pro Asp Ala Phe Val Thr Met Thr Gly Gly
Phe Arg Arg Gly Lys Lys Ile Gly His Asp Val Asp
Phe Leu Ile Thr Ser Pro Gly Ser Ala Glu Asp Glu
Glu Gln Leu Leu Pro Lys Val Ile Asn Leu Trp Glu
Lys Lys Gly Leu Leu Leu Tyr Tyr Asp Leu Val Glu
Ser Thr Phe Glu Lys Phe Lys Phe Thr Leu Pro Ser
Arg Gln Val Asp Thr Leu Asp His Phe Gln Lys Cys
Phe Leu Ile Leu Lys Leu His His Gln Arg Val Asp
Ser Ser Lys Ser Asn Gln Gln Glu Gly Lys Thr Trp
Lys Ala Ile Arg Val Asp Leu Val Met Cys Pro Tyr
Glu Asn Arg Ala Phe Ala Leu Leu Gly Trp Thr Gly
Ser Arg Gln Phe Glu Arg Asp Ile Arg Arg Tyr Ala
Thr His Glu Arg Lys Met Met Leu Asp Asn His Ala
Leu Tyr Asp Lys Thr Lys Arg Val Phe Leu Lys Ala
Glu Ser Glu Glu Glu Ile Phe Ala His Leu Gly Leu
Asp Tyr Ile Glu Pro Trp Glu Arg Asn Ala

TABLE 6

Nucleotide Sequence of a 4151 and His-tagged Bovine TdT.

SEQ ID No. 6: (1148 nt)

```
atgagaggat cgcatcacca tcaccatcac aagactccac
cacttgctgt aaaaaagatc tcccagtacg cgtgtcaaag
aaaaaccact tgaacaact ataaccacat attcacggat
gcctttgaga tactggctga aaattctgag tttaaagaaa
atgaagtctc ttatgtgaca tttatgacag cagcttctgt
acttaaatct ctgccattca caatcatcag tatgaaggat
acagaaggaa ttccctgcct ggggacaag gtgaagtgta
tcatagagga aattattgaa gatggagaaa gttctgaagt
taaagctgtg ttaaatgatg aacgatatca gtccttcaaa
ctctttactt ctgttttttg agtgggactg aagacatctg
agaaatggtt caggatgggg ttcagatctc tgagtaaaat
aatgtcagac aaaaccctga aattcacaaa aatgcagaaa
gcaggatttc tctattatga agaccttgtc agctgcgtga
ccagggccga agcagaggcg gttggcgtgc tggttaaaga
ggctgtgtgg gcatttctgc cggatgcctt tgtcaccatg
acaggaggat tccgcagggg taagaagatt gggcatgatg
tagatttttt aattaccagc ccaggatcag cagaggatga
agagcaactt ttgcctaagg tgataacct atgggaaaa
aaggattac ttttatatta tgaccttgtg gagtcaacat
ttgaaaagtt caagttgcca agcaggcagg tggatacttt
agatcatttt caaaaatgct ttctgatttt aaaattgcac
catcagagag tagacagtag caagtccaac cagcaggaag
gaaagacctg gaaggccatc cgtgtgacc tggttatgtg
cccctacgag aaccgtgcct tgcccgct aggctggact
ggctccggc agtttgagag agacatccgg cgctatgcca
cacacgagcg gaagtgatg ctggataacc acgctttata
tgacaagacc aagagggtat ttctcaaagc ggaaagtgaa
gaagaaatct ttgcacatct gggattggac tacattgaac
catgggaag aaatgcttaa gcttgcgc
```

TABLE 8

Nucleotide Sequence of a 4160 and His-tagged Bovine TdT.

SEQ ID No. 8: (1121 nt)

```
atgagaggat cgcatcacca tcaccatcac atctcccagt
acgcgtgtca agaaaaaccc actttgaaca actataacca
catattcacg gatgcctttg agatactggc tgaaaattct
gagtttaaag aaaatgaagt ctcttatgtg acatttatga
gagcagcttc tgtacttaaa tctctgccat tcacaatcat
cagtatgaag gatacagaag gaattccctg cctgggggac
aaggtgaagt gtatcataga ggaaattatt gaagatggag
aaagttctga agttaaagct gtgttaaatg atgaacgata
tcagtccttc aaactctttta cttctgtttt tggagtggga
ctgaagacat ctgagaaatg gttcaggatg gggttcagat
ctctgagtaa aataatgtca gacaaaaccc tgaaattcac
aaaaatgcag aaagcaggat ttctctatta tgaagacctt
gtcagctgcg tgaccaggc cgaagcagag gcggttggcg
tgctggttaa agaggctgtg tgggcatttc tgccggatgc
ctttgtcacc atgacaggag gattccgcag gggtaagaag
attgggcatg atgtagattt tttaattacc agcccaggat
cagcagagga tgaagagcaa cttcttccta aagtgataaa
cttatgggaa aaaaaggat tactttttata ttatgacctt
gtggagtcaa catttgaaaa gttcaagttg ccaagcaggc
aggtggatac ttttagatcat tttcaaaaat gctttctgat
tttaaaattg caccatcaga gagtagacag tagcaagtcc
aaccagcagg aaggaaagac ctggaaggcc atccgtgtgg
acctggttat gtgccctac gagaaccgtg ccttgcccct
gctaggctgg actggctccc ggcagtttga gagagacatc
cggcgctatg ccacacgctt tatatgacaag accaagaggg
accacgcttt atatgacaag accaagaggg tatttctcaa
agcggaaagt gaagaagaaa tctttgcaca tctgggattg
gactacattg aacccatggga agaaatgct taagcttgcg c
```

TABLE 9

Amino Acid Sequence of murine TdT

SEQ ID NO. 9: (510 aa)

```
MDPLQAVHLG PRKKRPRQLG TPVASTPYDI RFRDLVLFIL
EKKMGTTRRA FLMELARRKG FRVENELSDS VTHIVAENNS
GSDVLEWLQL QNIKASSELE LLDISWLIEC MGAGKPVEMM
GRHQLVVNRN SSPSPVPGSQ NVPAPAVKKI SQYACQRRTT
LNNYNQLFTD ALDILAENDE LRENEGSCLA FMRASSVLKS
LPFPITSMKD TEGIPCLGDK VKSIIEGIIE DGESSEAKAV
LNDERYKSFK LFTSVFGVGL KTAEKWFRMG FRTLSKIQSD
KSLRFTQMQK AGFLYYEDLV SCVNRPEAEA VSMLVKEAVV
TFLPDALVTM TGGFRRGKMT GHDVDFLITS PEATEDEEQQ
LLHKVTDFWK QQGLLLYCDI LESTFEKFKQ PSRKVDALDH
FQKCFLILKL DHGRVHSEKS GQQEGKGWKA IRVDLVMCPY
DRRAFALLGW TGSRQFERDL RRYATHERKM MLDNHALYDR
TKRVFLEAES EEEIFAHLGL DYIEPWERNA
```

In certain embodiments, modified enzymes of the invention may include an N-terminus truncation relative to their respective native TdT enzyme. For example, in preferred embodiments, the native enzyme may be murine TdT as provided in SEQ ID NO. 9 above. The modified TdT may be truncated at the equivalent of position 147 or 131 of the native murine TdT as shown in SEQ ID Nos. 10 and 11 respectively. Modified TdTs may include a protein tag sequence such as a His tag and additional linkers at their N-terminus as illustrated in SEQ ID Nos. 10 and 11. The His-tag portion if underlined in each of the sequences and the linker is provided in bold.

SEQ ID No. 10: Murine del-147 with His-tag and linker
MRGSHHHHHHGMASMTGGQQMGRDLYDDDDKDRWGSELEKKISQYACQRR

TTLNNYNQLFTDALDILAENDELRENEGSCLAFMRASSVLKSLPFPITSM

KDTEGIPCLGDKVKSIIEGIIEDGESSEAKAVLNDERYKSFKLFTSVFGV

GLKTAEKWFRMGFRTLSKIQSDKSLRFTQMQKAGFLYYEDLVSCVNRPEA

EAVSMLVKEAVVTFLPDALVTMTGGFRRGKMTGHDVDFLITSPEATEDEE

QQLLHKVTDFWKQQGLLLYCDILESTFEKFKQPSRKVDALDHFQKCFLIL

KLDHGRVHSEKSGQQEGKGWKAIRVDLVMCPYDRRAFALLGWTGSRQFER

DLRRYATHERKMMLDNHALYDRTKRVFLEAESEEEIFAHLGLDYIEPWER

NA

SEQ ID No. 11: Murine del-131 with His-tag and linker
MRGSHHHHHHGMASMTGGQQMGRENLYFQGSPSPVPGSQNVPAPAVKKIS

QYACQRRTTLNNYNQLFTDALDILAENDELRENEGSCLAFMRASSVLKSL

PFPITSMKDTEGIPCLGDKVKSIIEGIIEDGESSEAKAVLNDERYKSFKL

FTSVFGVGLKTAEKWFRMGFRTLSKIQSDKSLRFTQMQKAGFLYYEDLVS

CVNRPEAEAVSMLVKEAVVTFLPDALVTMTGGFRRGKMTGHDVDFLITSP

EATEDEEQQLLHKVTDFWKQQGLLLYCDILESTFEKFKQPSRKVDALDHF

QKCFLILKLDHGRVHSEKSGQQEGKGWKAIRVDLVMCPYDRRAFALLGWT

GSRQFERDLRRYATHERKMMLDNHALYDRTKRVFLEAESEEEIFAHLGLD

YIEPWERNA

Additional TdT modifications that may increase incorporation efficiency of 3'-O-blocked or other nucleotide analogs are listed in Table 10 below. While the modifications are described with referenced to the murine TdT listed in SEQ ID NO. 9, such the invention contemplates such modifications applied to the equivalent amino acids in any TdT including the truncated enzymes disclosed in SEQ ID Nos. 10 and 11 above with or without the His-tags and linkers. In various embodiments, contemplated modifications include deletion of the S420 through E424 amino acids. Various combinations of amino acid substitutions of the invention are listed in each row 1-175 of Table 10.

TABLE 10

| | | | | | | |
|---|---|---|---|---|---|---|
| 1 | A446S | | | | | |
| 2 | A446T | W450H | | | | |
| 3 | A446T | | | | | |
| 4 | A510G | | | | | |
| 5 | E177D | E180D | | | | |
| 6 | E177D | | | | | |
| 7 | E177K | E180K | R454A | | | |
| 8 | E177K | E180K | | | | |
| 9 | E177K | | | | | |
| 10 | E177S | | | | | |
| 11 | E180C | | | | | |
| 12 | E180D | E177D | W450H | | | |
| 13 | E180D | L189M | M192E | L381K | | |
| 14 | E180D | L189M | M192E | L381K | W450H | R454A | R461Q |
| 15 | E180D | M192E | L381K | R454T | R461Q | |
| 16 | E180D | M192E | L381Q | R454K | N474A | |
| 17 | E180D | M192E | R454K | | | |
| 18 | E180D | M192E | L381K | R454K | R461Q | N474R |
| 19 | E180D | M192K | L381Q | R454T | N474K | |
| 20 | E180D | W450Y | | | | |
| 21 | E180G | | | | | |
| 22 | E180K | L381K | W450H | R454A | N474A | |
| 23 | E180K | L381Q | W450H | R461V | | |
| 24 | E180K | M192E | L381K | R454T | N474K | |
| 25 | E180K | M192E | L381A | W450H | R454T | R461V |
| 26 | E180K | M192E | L381K | W450H | R454I | R461Q | N474R |
| 27 | E180K | M192E | L381V | N474A | | |
| 28 | E180K | M192E | L381W | R454I | R461V | |
| 29 | E180K | M192E | R454I | | | |
| 30 | E180K | M192E | R454T | | | |
| 31 | E180K | M192K | G337D | L381R | R454I | N474K |
| 32 | E180K | M192K | L381A | R454A | R461Q | N474K |
| 33 | E180K | M192K | L381A | R454K | N474K | |
| 34 | E180K | M192K | L381K | R454K | N474R | |
| 35 | E180K | M192K | L381K | R454T | N474K | |
| 36 | E180K | M192K | L381K | W450H | R454I | N474R |
| 37 | E180K | M192K | L381R | W450H | R461V | N474R |
| 38 | E180K | M192K | R454I | | | |
| 39 | E180K | M192K | R454K | R461V | N474R | |
| 40 | E180K | M192P | R454T | | | |
| 41 | E180K | M192W | L381A | R454I | R461Q | N474K |
| 42 | E180K | M192W | L381K | R454K | N474A | |
| 43 | E180K | M192W | L381R | W450H | | |
| 44 | E180K | M192W | L381R | W450H | R454K | R461Q |
| 45 | E180K | M192W | L381V | R454A | | |
| 46 | E180K | M192W | R454T | R461Q | | |
| 47 | E180K | R335K | | | | |
| 48 | E180K | R454A | | | | |
| 49 | E180K | R454I | R461V | | | |
| 50 | E180K | R454K | | | | |
| 51 | E180K | R454T | | | | |
| 52 | E180L | E226D | L381Q | R454A | R461V | N474A |
| 53 | E180L | L381A | R454A | R461Q | N474K | |
| 54 | E180L | L381A | R454I | R461Q | | |
| 55 | E180L | L381A | R454I | R461Q | N474K | |
| 56 | E180L | M192E | L381K | R461Q | N474K | |
| 57 | E180L | M192E | L381K | R461Q | N474K | |
| 58 | E180L | M192K | L381K | R454T | N474A | |
| 59 | E180L | W450H | R454T | R461Q | | |
| 60 | E33K | R307T | F187Y | | | |
| 61 | F405R | | | | | |
| 62 | F405Y | N474R | W450H | | | |
| 63 | F405Y | | | | | |
| 64 | K403S | | | | | |
| 65 | L347H | | | | | |
| 66 | L381I | N474R | | | | |
| 67 | L381K | R454K | | | | |
| 68 | L381Q | E180K | N474R | | | |
| 69 | L381Q | E180K | | | | |

TABLE 10-continued

| # | | | | | |
|---|---|---|---|---|---|
| 70 | L381Q | W450H | | | |
| 71 | L381Q | | | | |
| 72 | L381R | E180K | N474R | | |
| 73 | L381R | E180K | | | |
| 74 | L381R | N474R | | | |
| 75 | L381R | | | | |
| 76 | L381V | E180K | | | |
| 77 | L381V | N474R | | | |
| 78 | L381V | | | | |
| 79 | L381W | N474R | | | |
| 80 | L381W | R454T | R461V | N474R | |
| 81 | L381Y | W450H | | | |
| 82 | L398F | E180K | N474R | | |
| 83 | L398F | E180K | | | |
| 84 | L398F | N474R | | | |
| 85 | L398H | E180K | N474R | | |
| 86 | L398M | E180K | N474R | | |
| 87 | L398M | F405Y | | | |
| 88 | L398M | N474R | | | |
| 89 | L398M | W450H | | | |
| 90 | L472F | G449A | N474R | R454D | |
| 91 | L472F | N474R | R454D | E457A | |
| 92 | L472F | N474R | R454K | E457D | |
| 93 | L472F | N474R | R454Q | E457D | |
| 94 | L472F | N474R | R454Q | E457S | |
| 95 | L472F | R454K | E457D | R461A | |
| 96 | M192 | | | | |
| 97 | M192A | | | | |
| 98 | M192E | L381R | R454T | R461V | N474A |
| 99 | M192E | L381V | R454I | R461V | |
| 100 | M192E | L381V | R454I | R461V | N474K |
| 101 | M192E | L381V | W450H | R454K | |
| 102 | M192E | L381V | W450H | R454K | R461V | N474A |
| 103 | M192E | R454A | | | |
| 104 | M192G | | | | |
| 105 | M192H | | | | |
| 106 | M192K | L381Q | R454K | N474R | |
| 107 | M192K | L381Q | R461Q | N474K | |
| 108 | M192W | L381R | R454K | N474K | |
| 109 | Q390R | | | | |
| 110 | Q455A | R454G | | | |
| 111 | Q455E | | | | |
| 112 | Q455F | | | | |
| 113 | Q455H | | | | |
| 114 | Q455L | | | | |
| 115 | Q455M | | | | |
| 116 | Q455N | R454G | | | |
| 117 | Q455S | R454G | W450H | | |
| 118 | Q455T | R454G | | | |
| 119 | Q455T | | | | |
| 120 | R336N | H342R | | | |
| 121 | R454T | G337H | | | |
| 122 | R454T | G341C | | | |
| 123 | R432Q | D434H | R336Q | H342R | |
| 124 | R454C | | | | |
| 125 | R454E | | | | |
| 126 | R454G | Q455R | | | |
| 127 | R454H | W450H | | | |
| 128 | R454H | W450Y | | | |
| 129 | R454H | | | | |
| 130 | R454I | | | | |
| 131 | R454M | | | | |
| 132 | R454N | | | | |
| 133 | R454P | | | | |
| 134 | R454Q | | | | |
| 135 | R454S | | | | |
| 136 | R454T | T331A | | | |
| 137 | R454T | | | | |
| 138 | R454V | | | | |
| 139 | R461K | | | | |
| 140 | S453A | R454A | | | |
| 141 | S453G | R454A | W450H | | |
| 142 | S453G | W450H | | | |
| 143 | S453T | W450H | | | |
| 144 | S453T | | | | |
| 145 | T451S | | | | |
| 146 | T455V | | | | |
| 147 | T455Y | | | | |
| 148 | E457K | | | | |
| 149 | V436A | W450H | | | |
| 150 | V436A | | | | |
| 151 | L381Q | W450H | | | |
| 152 | E33K | W303H | | | |
| 153 | E180K | L381R | | | |
| 154 | N304K | | | | |
| 155 | N304R | | | | |
| 156 | N509K | | | | |
| 157 | N509R | | | | |
| 158 | D434K | | | | |
| 159 | D434R | | | | |
| 160 | D170K | | | | |
| 161 | D170R | | | | |
| 162 | D173K | | | | |
| 163 | D173R | | | | |
| 164 | E457K | | | | |
| 165 | E457R | | | | |
| 166 | D473K | | | | |
| 167 | D473R | | | | |
| 168 | Q402K | | | | |
| 169 | Q402R | | | | |
| 170 | D399K | | | | |
| 171 | D339L | | | | |
| 172 | E382K | | | | |
| 173 | E382R | | | | |
| 174 | Q455K | | | | |
| 175 | Q455R | | | | |

A variety of 3'-O-modified dNTPs and NTPs may be used with the disclosed proteins for de novo synthesis. In some embodiments, the preferred removable 3'-O-blocking group is a 3'-O-amino, a 3'-O-allyl or a 3'-O-azidomethyl. In other embodiments, the removable 3'-O-blocking moiety is selected from the group consisting of O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O[5-methyl]-tetrahydropyranyl; and O-tetrahydrothiofuranyl (see U.S. Pat. No. 8,133,669). In other embodiments the removable blocking moiety is selected from the group consisting of esters, ethers, carbonitriles, phosphates, carbonates, carbamates, hydroxylamine, borates, nitrates, sugars, phosphoramide, phosphoramidates, phenylsulfenates, sulfates, sulfones and amino acids (see Metzker M L et al. Nuc Acids Res. 1994; 22(20):4259-67, U.S. Pat. Nos. 5,763,594, 6,232,465, 7,414,116; and 7,279,563, all of which are incorporated by reference in their entireties).

Synthesis of Exemplary 3'-O-Blocked dNTP Analogs

FIG. 6 shows four exemplary 3'-O-blocked dNTP analogs, namely 3'-O-azidomethyl-dATP, 3'-O-azidomethyl-dCTP, 3'-O-azidomethyl-dGTP, and 3'-O-azidomethyl-dTTP. The synthesis of each 3'-O-azidomethyl analog is described below and detailed in FIGS. 7-12. The 3'-O-blocked dNTP analogs can also be purchased from specialty suppliers, such as Azco Biotech, Oceanside, Calif. It is to be understood that corresponding 3'-O-blocked ribonucleotides can be formed with similar synthetic methods to enable the creation of custom RNA oligos.

3'-O-azidomethyl-dATP: With reference to FIG. 7, a solution of $N^6$-benzoyl-5'-O-(tert-butyldimethylsilyl)-2'-deoxyadenosine (3.0 g; 6.38 mmol) [CNH Technologies, Woburn, Mass.] in DMSO (12 ml), acetic acid (5.5 ml) and acetic anhydride (17.6 ml) was prepared. The mixture was stirred at room temperature for 48 h. Approximately 100 ml of a saturated $NaHCO_3$ solution was added and the aqueous layer was extracted with $CH_2Cl_2$. The combined organic extract was washed with saturated $NaHCO_3$ solution and dried over $Na_2SO_4$. The residue was purified by flash column chromatography (hexane/ethyl acetate, 1:1 to 1:4) to recover N⁶-Benzoyl-3'-O-(methylthiomethyl)-5'-O-(tert-butyldimethylsilyl)-2'-deoxyadenosine (shown as compound 1 in FIG. 7) as a white powder (2.4 g; 71% yield). 400 mg of N⁶-Benzoyl-3'-O-(methylthiomethyl)-5'-O-(tert-butyldimethylsilyl)-2'-deoxyadenosine was dissolved in dry $CH_2Cl_2$ (7 ml) under nitrogen to create a solution (0.76 mmol). Cyclohexene (400 µl), and $SO_2Cl_2$ (155 µl; 1.91 mmol, redistilled) were then added. The reaction mixture was stirred at 0° C. for 2 h. The solvent was then removed under reduced pressure and then under a high-vacuum pump for 10 min. The resulting residue was dissolved in dry DMF (5 ml) and reacted with $NaN_3$ (400 mg; 6.6 mmol) at room temperature for 3 h. The reaction mixture was dispersed in distilled water (50 ml) and extracted with $CH_2Cl_2$. The combined organic layer was dried over $Na_2SO_4$ and concentrated under reduced pressure. The residue was dissolved in MeOH (5 ml) and stirred with $NH_4F$ (300 mg; 8.1 mmol) at room temperature for 24 h. The solvent was then removed under reduced pressure. The reaction mixture was concentrated under reduced pressure and partitioned between water and $CH_2Cl_2$. The organic layer was separated and dried over $Na_2SO_4$. After concentration, the crude product was purified by flash column chromatography (ethyl acetate/methanol) to produce N⁶-Benzoyl-3'-O-(azidomethyl)-2'-deoxyadenosine (compound 2; FIG. 7) as a white powder (150 mg; 48% yield). N⁶-Benzoyl-3'-O-(azidomethyl)-2'-deoxyadenosine (123 mg; 0.3 mmol) and a proton sponge (75.8 mg; 0.35 mmol) were then dried in a vacuum desiccator over $P_2O_5$ overnight before dissolving in trimethyl phosphate (600 µl). Next freshly distilled $POCl_3$ (40 µl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dATP (FIG. 7, compound 3), a nucleotide analog to be used for later synthesis.

3'-O-azidomethyl-dTTP: Acetic acid (4.8 ml) and acetic anhydride (15.4 ml) were added to a stirred solution of 5'-O-(tertbutyldimethylsilyl)thymidine (2.0 g; 5.6 mmol) [CNH Technologies, Woburn, Mass.] in DMSO. The reaction mixture was stirred at room temperature for 48 h. A saturated $NaHCO_3$ solution (100 ml) was added, and the aqueous layer was extracted with ethyl acetate (3×100 ml). The combined organic extract was washed with a saturated solution of $NaHCO_3$ and dried over $Na_2SO_4$. After concentration, the crude product was purified by flash column chromatography (hexane/ethyl acetate) to produce 3'-O-(Methylthiomethyl)-5'-O-(tert-butyldimethylsilyl)thymidine (FIG. 8; Compound 4) as a white powder (1.75 g; 75% yield). Approximately 1 gram of 3'-O-(Methylthiomethyl)-5'-O-(tert-butyldimethylsilyl)thymidine was then dissolved in dry $CH_2Cl_2$ (10 ml) under nitrogen. To this mixture cyclohexene (1.33 ml) and $SO_2Cl_2$ (2840; 3.5 mmol, redistilled) were added. The resulting mixture was then stirred at 0° C. for 1.5 h. The solvent was then removed under reduced pressure and then under high vacuum for 10 min. The residue was dissolved in dry DMF (5 ml) and reacted with $NaN_3$ (926 mg; 15.4 mmol) at room temperature for 3 h. That reaction mixture was next dispersed in distilled water (50 ml) and extracted with $CH_2Cl_2$ (3×50 ml). The combined organic extract was dried over $Na_2SO_4$ and concentrated under reduced pressure. The residue was dissolved in MeOH (5 ml) and reacted with $NH_4F$ (600 mg; 16.2 mmol) at room temperature for 24 h. The reaction mixture was concentrated under reduced pressure and partitioned between water and $CH_2Cl_2$. The organic layer was then separated and dried over $Na_2SO_4$. After concentration, the residue was purified by flash column chromatography (hexane/ethyl acetate) to produce 3'-O-(azidomethyl)thymidine (FIG. 8, Compound 5) as a white powder (550 mg; 71% yield). Next, the 3'-O-(azidomethyl)thymidine and a proton sponge (0.35 mmol) were dried in a vacuum desiccator over $P_2O_5$ overnight before dissolving in trimethyl phosphate (600 µl). Next, freshly distilled $POCl_3$ (400; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dTTP (FIG. 8, compound 6), a nucleotide analog to be used for later synthesis.

3'-O-azidomethyl-dCTP: Three and a half grams of N⁴-benzoyl-5'-O-(tert-butyldimethylsilyl)-2'-deoxycytidine [CNH Technologies, Woburn, Mass.] was added to 14.7 ml of DMSO to produce a 7.65 mmol solution. To this solution, acetic acid (6.7 ml) and acetic anhydride (21.6 ml) were added, and the reaction mixture was stirred at room temperature for 48 h. A saturated $NaHCO_3$ solution (100 ml) was then added and the aqueous layer was extracted with $CH_2Cl_2$ (3×100 ml). The combined organic extract was washed with a saturated solution of $NaHCO_3$ and then dried over $Na_2SO_4$. After concentration, the crude was purified by flash column chromatography (ethyl acetate/hexane) to produce N⁴-Benzoyl-3'-O-(methylthiomethyl)-5'-O-(tert-butyldimethylsilyl)-2'-deoxycytidine (FIG. 9; compound 7) as a white powder (2.9 g; 73% yield). In 8 ml of $CH_2Cl_2$ N⁴-Benzoyl-3'-O-(methylthiomethyl)-5'-O-(tert-butyldimethylsilyl)-2'-deoxycytidine (558 mg; 1.04 mmol) was dissolved and then cyclohexene (560 µl) and $SO_2Cl_2$ (220 µl; 2.7 mmol) were added. The reaction mixture was stirred at 0° C. for 1 h. The volatiles were then removed with reduced pressure. The remaining residue was dissolved in dry DMF (5 ml) and reacted with $NaN_3$ (400 mg; 6.6 mmol) at room temperature for 2 h. The reaction mixture was dispersed in distilled water (50 ml) and extracted with $CH_2Cl_2$ (3×50 ml). The combined organic extract was dried over $Na_2SO_4$ and concentrated under reduced pressure. The residue was dissolved in MeOH (5 ml) and reacted with $NH_4F$ (600 mg; 16.2 mmol) at room temperature for 24 h. The solvent was removed under reduced pressure. The resulting residue was suspended in water (50 ml) and extracted with $CH_2Cl_2$ (3×50 ml). The combined organic extract was dried over $Na_2SO_4$ and concentrated under reduced pressure. The crude product was purified by flash column chromatography (hexane/ethyl acetate) to produce $N^4$-Benzoyl-3'-O-(azidomethyl)-2'-deoxycytidine (FIG. 9, compound 8) as a white powder (200 mg; 50% yield). Next, the $N^4$-Benzoyl-3'-O-(azidomethyl)-2'-deoxycytidine and a proton sponge (0.35 mmol) were dried in a vacuum desiccator over $P_2O_5$ overnight before dissolving in trimethyl phosphate (600 µl). Then freshly distilled $POCl_3$ (400; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dCTP (FIG. 9, compound 9), a nucleotide analog to be used for later synthesis.

3'-O-azidomethyl-dGTP: To a stirred solution of $N^2$-isobutyryl-5'-O-(tert-butyldimethylsilyl)-2'-deoxyguanosine (5 g; 11.0 mmol) [CNH Technologies, Woburn, Mass.] in dry DMSO (21 ml), acetic acid (10 ml) and acetic anhydride (32 ml) were added. The reaction mixture was stirred at room temperature for 48 h. A saturated $NaHCO_3$ solution (100 ml) was added and the aqueous layer was extracted with ethyl acetate (3×100 ml). The combined organic extract was washed with a saturated $NaHCO_3$ solution and dried over $Na_2SO_4$. After concentration, the crude product was purified by flash column chromatography ($CH_2Cl_2$/MeOH) to produce $N^2$-Isobutyryl-3'-O-(methylthiomethyl)-5'-O-(tert-butyldimethylsilyl)-2'-deoxyguanosine (FIG. 10, compound 10) as a white powder (3.9 g; 69% yield). One gram of $N^2$-Isobutyryl-3'-O-(methylthiomethyl)-5'-O-(tert-butyldimethylsilyl)-2'-deoxyguanosine was subsequently added to dry pyridine (22 ml; 2.0 mmol) along with diphenylcarbamoyl chloride (677 mg; 2.92 mmol) and DIEA (N,N-diisopropylethylamine; SIGMA) (1.02 ml; 5.9 mmol). The reaction mixture was stirred under nitrogen atmosphere at room temperature for 3 h. The solvent was removed under high vacuum. The crude product was purified by flash column chromatography (ethyl acetate/hexane) to produce $N^2$-Isobutyryl-$O^6$-(diphenylcarbamoyl)-3'-O-(methylthiomethyl)-5'-O-(tert-butyldimethylsilyl)-2'-deoxyguanosine (FIG. 10, compound 11), which appeared as a yellowish powder (1.09 g; 80% yield). $N^2$-Isobutyryl-$O^6$-(diphenylcarbamoyl)-3'-O-(methylthiomethyl)-5'-O-(tert-butyldimethylsilyl)-2'-deoxyguanosine was then dissolved in dry $CH_2Cl_2$ (1.1 mmol) and stirred under nitrogen atmosphere at 0° C. for 1.5 h. The solvent was removed under reduced pressure and then under high vacuum for 10 min. The resulting residue was dissolved in dry DMF (5 ml) and reacted with $NaN_3$ (600 mg; 10 mmol) at room temperature for 3 h. The reaction mixture was then dispersed in distilled water (50 ml) and extracted with $CH_2Cl_2$ (3×50 ml). The combined organic extract was dried over $Na_2SO_4$ and concentrated under reduced pressure. The resultant residue was dissolved in MeOH (5 ml) and reacted with $NH_4F$ (500 mg; 13.5 mmol) at room temperature for 24 h. The solvent was removed under reduced pressure. The residue was suspended in water (50 ml) and extracted with $CH_2Cl_2$ (3×50 ml). The combined organic extract was dried over $Na_2SO_4$ and concentrated under reduced pressure. The crude product was purified by flash column chromatography (hexane/ethyl acetate) to produce $N^2$-Isobutyryl-$O^6$-(diphenylcarbamoyl)-3'-O-azidomethyl-2'-deoxyguanosine (FIG. 10, compound 12) as a white powder (230 mg; 36% yield). Finally, the $N^2$-Isobutyryl-$O^6$-(diphenylcarbamoyl)-3'-O-azidomethyl-2'-deoxyguanosine and a proton sponge (0.35 mmol) were dried in a vacuum desiccator over $P_2O_5$ overnight before dissolving in trimethyl phosphate (600 µl). Then freshly distilled $POCl_3$ (400; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dGTP (FIG. 10, compound 13), a nucleotide analog to be used for later synthesis.

As described with respect to FIG. 2, once a 3'-O-blocked dNTP or 3'-O-blocked rNTP is added, it will be necessary to remove the blocking group so that additional dNTPs or rNTPs can be added. In some embodiments, the 3'-O-blocking group can be removed with a palladium catalyst in neutral aqueous solution at elevated temperature hydrochloric acid to pH 2, a reducing agent such as mercaptoethanol, or by the addition of tris-(2-carboxyethyl) phosphine. See, e.g., U.S. Pat. No. 6,664,079; Meng, et al. *J. Org. Chem.,* 2006, 71(81):3248-52; Bi et al., *J. Amer. Chem. Soc.* 2006; 2542-2543, U.S. Pat. Nos. 7,279,563, and 7,414,116, all of which are incorporated herein by reference in their entireties. In other embodiments, the 3'-substitution group may be removed by UV irradiation (see, e.g., WO 92/10587, incorporated by reference herein in its entirety). Most 3'-O-blocking groups are removed by oxidative, reductive or hydrolytic chemical reactions. In some embodiments, a 3'-O—NO2 group is removed from a oligonucleotide by a 40% w/v solution of ammonium sulfide for <5 minutes at R.T. In some embodiments, a 3'-O—CH2CN group is removed from an oligonucleotide by treatment with 0.5M KOH at 70° C. In some embodiments, the removal of the 3'-O-blocking group does not include chemical cleavage but uses a cleaving enzyme such as alkaline phosphatase.

In preferred embodiments an enzymatic reaction is used for removal of the 3'-blocking group. Shrimp Alkaline Phosphatase (SAP) may be used in certain embodiments. SAP has one of the fastest enzymatic rates reported in the literature and has a wide range of substrate utilization.

3'-O-Methoxymethyl-dTTP: 5'-O-Benzoylthymidine (173 mg, 0.5 mmol, 1 equiv) was dissolved in 10 mL of dichloromethane under argon at ambient T. Di-isopropylethylamine (128 mg, 1 mmol, 2 equiv) was added followed by methoxymethyl bromide (124 mg, 1 mmol, 2 equiv). The mixture was stirred at ambient T for 18h. The mixture was diluted with 10 mL dichloromethane and this was washed successively with 20 mL of 5% aq HCl, and brine. The organic layer was dried with sodium sulfate and evaporated. 5'-O-Benzoyl-3'-O-methoxymethylthymidine (50 mg, 0.13 mmol) was dissolved in 5 mL of concentrated ammonium hydroxide at ambient temperature. The mixture was stirred at ambient T overnight. The mixture was diluted extracted 3 times with 10 mL portions of dichloromethane. The combined extracts were washed with brine. The organic layer was dried with sodium sulfate and evaporated. 3'-O-Methoxymethylthymidine (23 mg, 0.08 mmol) was co-evaporated with pyridine (1.5 mL×3) and dried overnight under high vacuum. The nucleoside was dissolved in a mixture of 1.5 mL of trimethylphosphate and 0.6 mL dry pyridine under Ar. The mixture was cooled in an ice bath. a first aliquot of 10 uL of POCl$_3$ was added dropwise. Five minutes later, a second aliquot of 10 uL was added. The mixture was stirred an additional 30 min. A solution of the TBA phosphate salt in dry DMF (1.25 mL) was cooled in an ice bath in a vial under Ar. This was added to the rxn mixture dropwise over 10 sec. Immediately the pre-weighed solid proton sponge (21 mg, 1.25 equiv) was added as a solid in one portion. The mixture was stirred for 25 min after this addition and was quenched with 5 mL of cold TEAB buffer. The mixture was stirred in the ice bath for 10 min and then transferred to a small RB flask for FPLC separation. Final separation was accomplished by reverse phase HPLC using a water/acetonitrile gradient containing 0.1 mM formic acid.

3'-O-Methylthiomethyl-dCTP: To a suspension of deoxycytidine (1 g, 4.4 mmol) in 25 mL of methanol was added N,N-dimethylformamide dimethyl acetal (1.75 mL, 13.2 mmol). The mixture was stirred overnight at ambient temperature. The reaction mixture was evaporated, and the residue was purified by flash chromatography using a DCM/methanol gradient as eluant. N6-Formamidino-5'-O-benzoyldeoxy-3'-O-methylthiomethyldeoxycytidine (250 mg, 0.41 mmol) was dissolved in 10 mL of methanol and 10 mL conc aqueous ammonium hydroxide. The mixture was stirred at ambient temperature for 18 h and then evaporated under reduced pressure. The residue was purified by column chromatography (DCM/Methanol 98:2 to 90:10) to afford 170 mg (93%) of the desired nucleoside as a slightly yellow solid. 3'-O-Methylthiomethyl dexoxycytidine (25.0 mg, 0.09 mmol) in a 25 mL vial was co-evaporated with anhydrous pyridine (3×1 mL) and dried over the weekend. Trimethyl phosphate (0.7 mL) was added to dissolve the nucleoside and cooled in an ice bath to 0° C. Phosphoryl chloride (28 µL, 0.3 mmol) was added slowly (12 µL, 5 min later 8 µL, 30 min later 8 µL) and the reaction was stirred for 2 h at 0° C. The di(tetrabutylammonium) hydrogen pyrophosphate was dissolved in anhydrous DMF (1 mL), this mixture was cooled to 0° C. and added to the reaction mixture. Proton sponge (9.2 mg, 0.04 mmol) was added and the reaction was stirred at 0° C. for 2 h. To the reaction mixture was added 1 M triethylammonium bicarbonate buffer (TEAB) (2 mL) and the mixture was stirred for 1 h. The mixture was then transferred to round-bottom flask, 50 mL×3 of miliQ water was added and mixture was concentrated to dryness. The residue was dissolved in miliQ water (11 mL) and loaded onto an AKTA FPLC at room temperature. The fractions containing the triphosphate (F48-F52) were evaporated under reduced pressure at 40° C., and the residue was then lyophilized. The triphosphate was dried to afford the desired triphosphate (12 mg, 16.5%).

EXAMPLES

Example 1: Protein Modifications

Murine (mur) TdT variants originated from 380 aa synthetic gene. This backbone is a truncated version of WT murine TdT and represents a catalytic core of the ET sequence. Chemically synthesized TdT constructs were cloned into a pRSETA bacterial expression vector, featuring an N-terminal 6x-histidine tag and enterokinase cleavage site (ThermoFisher Scientific GeneArt Gene Synthesis). Synthetic TdT plasmids were maintained in DH5alpha cells (Biopioneer) plated on LB agar plates containing 100 ug/ml carbenicillin. For expression, the pRSETA-murine TdT plasmids were transformed into BL21 (DE3) pLysS cells (Thermo-Fisher) by incubating plasmids and cells on ice for 20 min., followed by a 30 sec. heat shock at 42° C., followed by addition of SOC media and incubation with shaking at 37° C. for 30-60 min. After addition of SOC media to cells, the entire volume (typically 60 ul) were plated on LB agar plates containing 100 ug/mL carbenicillin plus 34 ug/mL chloramphenicol.

Cells from 10 mL cultures (24-well plates, Corning) were harvested by centrifugation (3000×g, 15 min), then lysed in B-PER lysis buffer (Thermo-Fisher) containing lysozyme, protease inhibitors, and 100 mM NaCl. Pellets were soaked 1×60 min. in TBS buffer and supernatants collected for purification. The supernatant was bound onto 50 uL Ni-NTA bead (GE Life Sciences) slurry in 24-well plates for 30 min. The bead slurry was then washed 3×50 mM Tris-HCl, pH 8, 500 mM NaCl (500 uL), followed by washing 4×50 mM Tris-HCl, pH 8, 500 mM NaCl, 50 mM Imidazole (200 uL). The protein was then recovered by treating with 50 mM Tris-HCl, pH 8, 500 mM NaCl, 300 mM Imidazole (50 uL), then 50 mM Tris-HCl, pH 8, 500 mM NaCl, 300 mM Imidazole (130 uL), and finally 50 mM Tris-HCl, pH 8, 500 mM NaCl, 1M Imidazole (50 uL).

Recovered fractions were analyzed by taking 2.5 ul sample and running on 8% NuPage gel (Thermo-Fisher), 200 V for 50 min, denaturing conditions. Gel stained with Coomassie Blue. The eluted protein was buffer exchanged using a 7.5 MWCO desalting column (Thermo-Fisher) and sored at −80° C. (Storage Buffer=20 mM Tris-HCl, pH 6.8, 50 mM NaOAc; 0.01% Triton X-100 and 10% Glycerol).

Activity Screens:

TdT activity screening was performed via a dNTP polymerase extension reaction using different 3'-O-blocked dNTP analogs and a biotinylated oligonucleotide:

SEQ ID NO. 12
5BiosG/TAATAATAATAATAATAATAATAATAATAATAATTTTTT
(ChemGenes Corporation)

Reactions were typically set up in a 96 well plate. Reactions were performed by making a master mix with final concentrations of the following components: 0.2 U PPase (Thermo-Fisher), 10 pmol of oligonucleotide, 75 uM dNTP (see below), 1×TdT reaction buffer (5× from Thermo-Fisher) to a final volume of 10 ul. Reactions were initiated by adding a defined volume (typically 2 ul) of TdT variants in different wells and incubating the reaction mix at 37° C. for 5 min and 60 min time points. Reactions were terminated by removal of a 10 ul aliquot and adding to 5 ul of 250 mM EDTA.

dNTPs Tested:

| | |
|---|---|
| 3'-O-azidomethyl-dTTP | see description above |
| 3'-O-azidomethyl-dATP | see description above |
| 3'-O-azidomethyl-dGTP | see description above |
| 3'-O-MOM-dTTP | see description above |
| 3'-O-MTM-dCTP | see description above |
| 3'-aminoxy-dTTP | Firebird BioMolecular Sciences LLC |
| 3'-aminoxy-dATP | Firebird BioMolecular Sciences LLC |
| 3'-aminoxy-dGTP | Firebird BioMolecular Sciences LLC |
| 3'-O-methyl-dATP | TriLink BioTechnologies LLC |
| 3'-O-methyl-dGTP | TriLink BioTechnologies LLC |
| 3'-O-methyl-dCTP | TriLink BioTechnologies LLC |

Biotinylated oligos in the quenched reaction mix were bound to Streptavidin beads (0.77 um, Spherotech). The beads were then transferred to filter plates (Pall Corporation) and washed several times with water. The oligonucleotides were cleaved from the solid support by incubating the plate with cleavage buffer (10% Diisopropyl-amine in methanol) at 50° C. for 30 min followed by elution in water. The eluted samples were dried and dissolved in 30 µl of water containing oligonucleotide sizing standards (two oligonucleotides (ChemGenes Corporation) that are approximately 15-20 bases smaller or larger than the starting 42-mer oligonucleotide). Oligonucleotides were then analyzed for extension efficiency by Capillary Gel Electrophoresis (Oligo Pro II, Advanced Analytical Technologies Inc.).

Example 2: In Silico Modeling

Several amino acid modifications to the GGFRR and TGSR motifs and flanking amino acids discussed above were modeled in silico to determine modifications capable of increased incorporation of 3'-O-blocked dNTP analogs as described above. Single, double, and triple amino acid substitutions as well amino acid insertions were modeled. Table 11 below shows modifications found to elicit increased incorporation. Amino acid positions are provided with reference to murine TdT but are applicable to conserved sequences of any TdT. Rows in Table 11 describe a base modification to one or more amino acids in or flanking the GGFRR motif. Columns include additional combinations of modifications to other amino acids such as those in and flanking the TGSR motif.

TABLE 11

| Residue Position | Single Site Mutation | Combination with E180K | Combination on with R454T | Combination with E180K and R454T | Combination with R461V | Combination with N474R |
|---|---|---|---|---|---|---|
| T331 | T331M, T331S, T331A, T331V, T331G, T331I, T331N, T331C, T331L | T331M + E180K, T331S + E180K, T331A + E180K, T331V + E180K, T331G + E180K, T331I + E180K, T331N + E180K, T331C + E180K, T331L + E180K | T331M + R454T, T331S + R454T, T331A + R454T, T331V + R454T, T331G + R454T, T331V + R454T, T331I + R454T, T331N + R454T, T331C + R454T, T331L + R454T | T331M + E180K + R454T, T331S + R454T, T331S + E180K + R454T, T331A + R454T, T331A + E180K + R454T, T331G + E180K + R454T, T331I + R454T, T331G + E180K + R454T, T331I + E180K + R454T, T331N + E180K + R454T, T331C + E180K + R454T, T331L + E180K + R454T | T331M + R461V, T331S + R461V, T331A + R461V, T331V + R461V, T331G + R461V, T331I + R461V, T331N + R461V, T331C + R461V, T331L + R461V | T331M + N474R, T331S + N474R, T331A + N474R, T331V + N474R, T331G + N474R, T331I + N474R, T331N + N474R, T331C + N474R, T331L + N474R |
| G332 | G332A | G332A + E180K | G332A + R454T | G332A + E180K + R454T | G332A + R461V | G332A + N474R |
| G333 | G333S, G333A, G333D, G333P, G333E | G333S + E180K, G333A + E180K, G333D + E180K, G333P + E180K, G333E + E180K | G333S + R454T, G333A + R454T, G333D + R454T, G333P + R454T, G333E + R454T | G333S + E180K + R454T, G333A + E180K + R454T, G333D + E180K + R454T, G333P + E180K + R454T, G333E + E180K + R454T | G333S + R461V, G333A + R461V, G333D + R461V, G333P + N461V, G333E + N461V | G333S + N474R, G333A + N474R, G333D + N474R, G333P + N474R, G333E + N474R |
| G333 and F334 | G333S + F334Y | G333S + F334Y + E180K | G333S + F334Y + R454T | G333S + F334Y + E180K + R454T | G333S + F334Y + R461V | G333S + F334Y + N474R |
| F334 | F334H, F334Y, F334N | F334H + E180K, F334Y + E180K, F334N + E180K | F334H + R454T, F334Y + R454T, F334N + R454T | F334H + E180K + R454T, F334Y + E180K + R454T, F334N + E180K + R454T | F334H + R461V, F334Y + R461V, F334N + R461V | F334H + N464R, F334Y + N474R, F334N + N474R |

TABLE 11-continued

| Residue Position | Single Site Mutation | Combination with E180K | Combination on with R454T | Combination with E180K and R454T | Combination with R461V | Combination with N474R |
|---|---|---|---|---|---|---|
| F334 and Y insertion between F334 and R335 | F334S + 334_335insY | F334S + 334_335insY + E180K | F334S + 334_335insY + R454T | F334N + E180K + R454T, F334S + 334_335insY + E180K + R454T | F334S + 334_335insY + R461V | F334S + 334_335insY + N474R |
| R335 | R335L, R335S, R335K, R335W, R335T | R335L + E180K, R335S + E180K, R335K + E180K, R335W + E180K, R335P + E180K | R335L + R454T, R335S + R454T, R335K + R454T, R335W + R454T, R335T + R454T | R335L + E180K + R454T, R335S + E180K + R454T, R335K + E180K + R454T, R335W + E180K + R454T, R335T + E180K + R454T | R335L + R461V, R335S + R461V, R335K + R461V, R335W + R461V, R335T + R461V | R335L + N474R, R335S + N474R, R335K + N474R, R335W + N474R, R335T + N474R |
| R336 | R336K, R336S, R336I, R336N, R336V, R336Q | R336K + E180K, R336S + E180K, R336I + E180K, R336N + E180K, R336V + E180K, R336Q + E180K | R336K + R454T, R336S + R454T, R336I + R454T, R336N + R454T, R336V + R454T, R336Q + R454T | R336K + E180K + R454T, R336S + E180K + R454T, R336I + E180K + R454T, R454N + E180K + R454T, R336V + E180K + R454T, R336Q + E180K + R454T | R336K + R461V, R336S + R461V, R336I + R461V, R336N + R461V, R336V + R461V, R336Q + R461V | R336K + N474R, R336S + N474R, R336I + N474R, R336N + N474R, R336V + N474R, R336Q + N474R |
| G337 | G337K, G337E, G337A, G337D, G337H, G337S | G337K + E180K, G337E + E180K, G337A + E180K, G337D + E180K, G337H + E180K, G337S + E180K | R337K + R454T, R337E + R454T, G337A + R454T, G337D + R454T, G337H + R454T, G337S + R454T | R336K + E180K + R454T, R336S + E180K + R454T, R336I + E180K + R454T, R454N + E180K + R454T, R336I + E180K + R454T, R336V + E180K + R454T, R336Q + E180K + R454T | G337K + R461V, G337E + R461V, G337A + R461V, G337D + R461V, G337H + R461V, G337S + R461V | G337K + N474R, G337E + N474R, G337A + N474R, G337D + N474R, G337H + N474R, G337S + N474R |
| K338 | K338R, K338A | K338R + E180K, K338A + E180K | K338R + R454T, K338A + R454T | K338R + E180K + R454T, K338A + E180K + R454T | K338R + R461V, K338A + R461V | K338R + N474R, K338A + N474R |
| G341 | G341C, G341S, G341V, G341I | G341C + E180K, G341S + E180K, G341V + E180K, G341I + E180K | G341C + R454T, G341S + R454T, G341V + R454T, | G341C + E180K + R454T, G341S + E180K + R454T, G341V + E180K + R454T, | G341C + R461V, G341S + R461V, G341V + R461V, | G341C + N474R, G341S + N464R, G341V + N474R, |

TABLE 11-continued

| Residue Position | Single Site Mutation | Combination with E180K | Combination with R454T | Combination with E180K and R454T | Combination with R461V | Combination with N474R |
|---|---|---|---|---|---|---|
| | | | G341I + R454T | G341V + E180K + R454T, G341I + E180K + R454T | G341I + R461V | G341I + N474R |
| H342 | H342G, H342K, H342R, H342D | H342G + E180K, H342K + E180K, H342R + E180K, H342D + E180K | H342G + R454T, H342K + R454T, H342R + R454T, H342D + R454T | H342G + E180K + R454T, H342K + E180K + R454T, H342R + E180K + R454T, H342D + E180K + R454T | H342G + R461V, H342K + R461V, H342R + R461V, H342D + R461V | H342G + N474R, H342K + N474R, H342R + N474R, H342D + N474R |

Example 3: Incorporation of dNTPs with Phosphate Blocking Groups

DNA and the nucleotides that comprise DNA are highly negatively charged due to the phosphate groups within the nucleotides. See Lipfert J, Doniach S, Das R, Herschlag D. Understanding Nucleic Acid-Ion Interactions, Annu Rev Biochem. 2014; 83: 813-841, incorporated herein by reference. 3'-PO4-dNTPs have an even greater negative charge relative to natural nucleotides due to the additional phosphate group at the 3'-position. The increased negative charge may affect the ability of the TdT to incorporate the modified nucleotides. In certain embodiments, engineered TdT enzymes of the invention may be modified for efficient incorporation of 3'-phosphate-dNTPs by neutralizing the negative charges with positive charges on the modified TdT.

The Average number of Neighboring Atoms Per Sidechain Atom (AvNAPSA) algorithm within the Rosetta protein software suite3 was used to identify mutations that will increase the positive charge in and around the enzymatic active site of TdT. By increasing a key parameter of the AvNAPSA algorithm, termed surface atom cutoff, sequence positions in the active site of TdT were targeted. The surface charge of proteins was manipulated by mutating solvent-exposed polar residues to charged residues, with the amount of solvent exposure determined by the number of neighboring non-self atoms. See, Miklos A E, et al., Structure-Based Design of Supercharged, Highly Thermoresistant Antibodies, Chemistry & Biology, Volume 19, Issue 4, 20 Apr. 2012, Pages 449-455; Kaufmann K W, et al., Practically useful: what the Rosetta protein modeling suite can do for you, Biochemistry. 2010 Apr. 13; 49(14):2987-98; the content of each of which is incorporate herein by reference. Increasing the surface_atom_cutoff term allows AvNAPSA to consider sequence positions with a higher number of neighboring atoms, such as positions within an enzyme active site. A summary of positions identified in TdT using AvNAPSA as being potentially useful for more efficient incorporation of 3'-phosphate-dNTP is shown in Table 12.

TABLE 12

TdT modifications for incorporation of phosphate-blocked dNTPs

| | |
|---|---|
| N304K | E457R |
| N304R | D473K |
| N509K | D473R |
| N509R | Q402K |
| D434K | Q402R |
| D434R | D399K |
| D170K | D339R |
| D170R | E382K |
| D173K | E382R |
| D173R | Q455K |
| E457K | Q455R |

FIGS. 13-16 illustrate the superior nucleotide incorporation of modified TdT over the wild type with respect to 3'-PO4-dNTPs. FIG. 13, Panel A is the CGE analysis of a chemically synthesized oligonucleotide (IDT) (21-mer; 5'-FAM-TAATAATAATAATAATTTTTT-PO$_4$-3'), while Panel B shows that the addition of one nucleotide bearing a 3'-PO$_4$ group, causes faster electrophoretic mobility than a comparable 20-mer (IDT) (5'-FAM-TAATAATA-ATAATAATTTTT). FIG. 14 is the CGE analysis demonstrating that Shrimp Akaline Phosphatase (SAP) (NEB #P0757) quantitatively removes a 3'-PO$_4$ group in 1 minute or less at a concentration of $1.23 \times 10^{-3}$ U/ul per pmol of oligonucleotide. The figure shows a titration series of increasing amounts of SAP from 0 U/ul (Panel A) to $1.0 \times 10^{-1}$ U/ul (Panel G). FIG. 15, Panel B is the CGE analysis of a murine WT TdT reaction mixture that demonstrates no polymerase mediated extension even in the presence of 500 uM 3'-PO$_4$-dTTP (MyChem LLC) as evidenced by no change to the starting material oligonucleotide shown in Panel A. Further evidence of the lack of substrate utilization of 3'-PO$_4$-dTTP is shown in panel C of FIG. 15 as demonstrated by the lack of reactivity of the oligonucleotide starting material (Panel A). FIG. 16 is a CGE analysis of the partial incorporation of a 3'-PO$_4$-dTTP by a variant TdT enzyme (E180K+M192K+L381K+R454K+N474R) as shown in panel B that demonstrates the appearance of a new oligonucleotide species (new peak circled) with a faster electrophoretic mobility as would be expected based on the results shown in FIG. 13. Further evidence of the incorporation of a 3'-PO$_4$ by the variant TdT is demonstrated by the post-extension removal of the 3'-PO$_4$ by treatment with SAP and the appearance of a new oligonucleotide species (Panel C—new peak circled) with an electrophoretic migration rate slower than the oligonucleotide starting material as would be expected from the poly-dT size ladder shown in panel D and the disappearance of the species formed in Panel B as indicated by the arrow in Panel C In another embodiment, increased incorporation of 3'-PO4-dTTP is demonstrated by a variant enzyme (E180K+M192K+R454K+R461V+N474R)

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A modified terminal deoxynucleotidyl transferase (TdT) comprising one or more mutations selected from the group consisting of E33K, E180L, E180K, M192E, M192K, M192W, W303H, L381K, L381Q, L381R, L381V, W450H, R454I, R454T, R454K, E457K, R461V, R461Q, R461V, N474R, and N474K, said modified TdT capable of adding a nucleotide analog comprising a removable blocking moiety at a 3'-Oxygen of the analog to a 3'-OH of a nucleic acid initiator in the absence of a nucleic acid template.

2. The modified TdT of claim 1, comprising a mutation E457K.

3. The modified TdT of claim 1, comprising the mutations E180K, M192W, L381R, and W450H.

4. The modified TdT of claim 1, comprising the mutations L381Q and W450H.

5. The modified TdT of claim 1, comprising the mutations E180L, M193E, L381K, R461Q, and N457K.

6. The modified TdT of claim 1, comprising the mutations E180K, L381Q, W450H and R461V.

7. The modified TdT of claim 1, comprising the mutations L381Q and W450H.

8. The modified TdT of claim 1, comprising the mutations E180L, M192E, L381K, R461Q, and N457K.

9. The modified TdT of claim 1, comprising the mutations E180K, M192E, L381K, R454T, and N47K.

10. The modified TdT of claim 1, comprising the mutations E180K, M192K, L381K, R454T, and N457R.

11. The modified TdT of claim 1, comprising the mutations E180K, M192K, L381K, R454K, and N457K.

12. The modified TdT of claim 1, comprising the mutations M192E, L381V, R454I, and R461V.

13. The modified TdT of claim 1, comprising the mutations E180K and L381R.

14. The modified TdT of claim 1, comprising the mutations E180K, M192K, L381K, R454K, and N474R.

15. The modified TdT of claim 1, wherein the modified TdT is capable of adding the nucleotide analog comprising the removable 3'-O-blocking moiety to the 3'-OH of the nucleic acid initiator at an increased rate compared to native TdT.

16. The modified TdT of claim 1, comprising an N-terminus truncation relative to native TdT.

17. The modified TdT of claim 15, wherein the modified TdT comprises an N-terminus t-131 murine TdT and a protein tag sequence attached to the N-terminus.

18. The modified TdT of claim 15, wherein the modified TdT comprises an N-terminus t-147 murine TdT and a protein tag sequence attached to the N-terminus.

19. The modified TdT of claim 1, wherein the modified TdT is capable of adding adenine, cytosine, guanine, and thymine deoxyribonucleotides modified with a removable 3'-O-blocking moiety.

20. The modified TdT of claim 18, wherein said nucleotides are 2'-deoxyribonucleotides.

21. The modified TdT of claim 1, wherein the modified TdT is capable of adding adenine, cytosine, guanine, and uracil ribonucleotides modified with a removable 3'-O-blocking moiety.

22. The modified TdT of claim 1, wherein said removable 3'-O-blocking moiety comprises a 3'-O-blocking group selected from the group consisting of CH2N3, NH2, ONHC(O)H, allyl, CH2SSCH3, phenoxyacetyl, methoxyacetyl, acetyl, (p-toluene)sulfonate, phosphate, nitrate, [4-methoxy]-tetrahydrothiopyranyl, tetrahydrothiopyranyl, [5-methyl]-tetrahydrofuranyl, [2-methyl,4-methoxy]-tetrahydropyranyl, [5-methyl]-tetrahydropyranyl; and O-tetrahydrothiofuranyl.

23. The modified TdT of claim 1, wherein the modified TdT is capable of incorporating a 3'-O-blocked nucleotide 5'-triphosphate, and said removable blocking moiety comprises a group selected from esters, ethers, carbonitriles, phosphates, carbonates, carbamates, hydroxylamine, borates, nitrates, sugars, phosphoramide, phosphoramidates, phenylsulfenates, sulfates, sulfones and amino acids.

24. The modified TdT of claim 1, wherein the modified TdT is capable of incorporating modified nucleotides at a reaction temperature from about 30° C. to about 80° C.

25. The modified TdT of claim 1, wherein the modified TdT is capable of incorporating modified nucleotides at a concentration of 1000 µM or less.

26. The modified TdT of claim 1, wherein the modified TdT is capable of incorporating modified nucleotides at a concentration of 100 µM or less.

27. The modified TdT of claim 14, said modified TdT capable of adding a nucleotide analog comprising a removable 3'-O-phosphate to the 3'-OH of a nucleic acid initiator.

* * * * *